(12) United States Patent
Ho

(10) Patent No.: US 8,667,964 B2
(45) Date of Patent: Mar. 11, 2014

(54) NASAL INTERFACE

(75) Inventor: Peter Chi Fai Ho, Pittsburgh, PA (US)

(73) Assignee: RIC Investments, LLC, Wilmington, DE (US)

( * ) Notice: Subject to any disclaimer, the term of this patent is extended or adjusted under 35 U.S.C. 154(b) by 1556 days.

(21) Appl. No.: 12/027,670

(22) Filed: Feb. 7, 2008

(65) Prior Publication Data

US 2008/0196728 A1 Aug. 21, 2008

Related U.S. Application Data

(60) Provisional application No. 60/901,790, filed on Feb. 16, 2007.

(51) Int. Cl.
*A62B 18/02* (2006.01)
*A62B 7/00* (2006.01)
*A61M 15/08* (2006.01)

(52) U.S. Cl.
USPC .............................. 128/207.13; 128/207.18

(58) Field of Classification Search
USPC ............. 128/206.25, 206.21, 206.24, 206.26, 128/207.13, 207.18, 206.11
See application file for complete search history.

(56) References Cited

U.S. PATENT DOCUMENTS

| | | | |
|---|---|---|---|
| 4,493,701 A | 1/1985 | Bootman et al. | |
| 4,753,233 A | 6/1988 | Grimes | |
| 5,335,656 A | 8/1994 | Bowe et al. | |
| 5,513,634 A | 5/1996 | Jackson | |
| 5,724,965 A * | 3/1998 | Handke et al. | 128/207.13 |
| 6,012,455 A * | 1/2000 | Goldstein | 128/207.18 |
| 6,439,234 B1 | 8/2002 | Curti et al. | |
| 2002/0157163 A1 | 10/2002 | Chen | |
| 2003/0217746 A1 | 11/2003 | Gradon et al. | |
| 2005/0076913 A1 | 4/2005 | Ho et al. | |
| 2006/0042632 A1 | 3/2006 | Bishop et al. | |
| 2006/0096598 A1 | 5/2006 | Ho et al. | |
| 2006/0107958 A1 | 5/2006 | Sleeper | |
| 2006/0137690 A1 | 6/2006 | Gunaratnam et al. | |
| 2006/0283461 A1 | 12/2006 | Lubke et al. | |

FOREIGN PATENT DOCUMENTS

| CN | 2235290 Y | 9/1996 |
|---|---|---|
| WO | WO2006026335 A2 | 3/2006 |

\* cited by examiner

*Primary Examiner* — Kristen Matter
(74) *Attorney, Agent, or Firm* — Michael W. Haas

(57) ABSTRACT

A patient interface includes a body portion configured to communicate with at least one fluid path, and at least one nostril interface extending from the body portion. The nostril interface includes an insertion portion configured to be inserted into a nostril of a patient and to be in communication with the at least one fluid path. In an embodiment, the insertion portion includes a plurality of laterally directed openings configured to communicate fluid between the fluid path and the nostril. The patient interface also includes a seal portion that is constructed and arranged to provide a seal between the patient interface and the nostril.

31 Claims, 13 Drawing Sheets

NASAL INTERFACE

CROSS-REFERENCE TO RELATED APPLICATIONS

This application claims priority under 35 U.S.C. §119(e) from provisional U.S. patent application No. 60/901,790 filed Feb. 16, 2007 the contents of which are incorporated herein by reference.

BACKGROUND OF THE INVENTION

1. Field of the Invention

The present invention relates to patient nasal interfaces for gas delivery, gas sampling, and/or combined gas delivery and sampling.

2. Description of the Related Art

Obstructive sleep apnea or OSA, obstructive sleep hypopnea, and upper airway resistance syndrome (UARS) are among a variety of known disorders characterized by episodes of complete or partial upper airway obstruction during a state of diminished consciousness, such as sleep, anesthetization, or post anesthesia. OSA, hypopnea, and UARS cause intermittent interruption of ventilation during sleep with the consequence of potentially severe oxyhemoglobin desaturation. Typically, those afflicted with OSA, hypopnea, and UARS experience repeated, frequent arousals from sleep in response to the oxygen deprivation. The arousals result in sleep fragmentation and poor sleep continuity.

Consequences of OSA, hypopnea, and UARS may include debilitating daytime sleepiness and cognitive dysfunction, systemic hypertension, cardiac dysrhythmias, pulmonary artery hypertension and congestive heart failure. Other consequences may include a predisposition to myocardial infarction, angina pectoris, stroke, right ventricular dysfunction with cor pulmonale, carbon dioxide retention during wakefulness as well as during sleep, and continuous, reduced arterial oxygen tension. Moreover, the cognitive impairment resulting from OSA, hypopnea, and UARS puts those afflicted at elevated risk of accidents.

The pathogenesis of the airway obstruction that characterizes OSA, hypopnea, and UARS can include both anatomic and functional abnormalities of the upper airway that result in increased air flow resistance. Such abnormalities may include narrowing of the upper airway due to suction forces created during inspiration, the effect of gravity pulling the tongue back towards the pharyngeal wall, and insufficient muscle tone in the upper airway dilator muscles, among others. It is also believed that excessive soft tissue in the anterior and lateral neck, as commonly observed in obese persons, can apply sufficient pressure to internal structures to narrow the upper airway and restrict air flow.

Conventional treatment of OSA, hypopnea, and UARS has included surgical intervention, such as uvalopalotopharyngoplasty, gastric surgery for obesity, mandibular advancement procedures, maxillo-facial reconstruction, and tracheostomy. However, surgery potentially involves considerable risk of post-operative morbidity and mortality. In addition, the failure rate of surgery is disturbingly high. Pharmacological therapy has also been proposed to treat OSA, hypopnea, and UARS; however, results have been generally disappointing.

More recently, continuous positive airway pressure (CPAP) or bi-level positive airway pressure applied during sleep has been used to treat OSA, hypopnea, and UARS patients. Positive pressure is applied in the upper airway to splint or support the airway open, thereby preventing its collapse and the resultant airway obstruction. A typical positive airway pressure device comprises a flow generator (e.g., a blower) that delivers gas via a delivery conduit to a patient interface, such as a mask. It is also known to deliver the positive airway pressure therapy as a continuous positive airway pressure (CPAP), a variable airway pressure, such as a bi-level pressure that varies with the patient's respiratory cycle (Bi-PAP), or an auto-titrating pressure that varies with the monitored condition of the patient. Pressure support therapies are also provided to treat other medical and respiratory disorders, such as Cheynes-Stokes respiration, congestive heart failure, and stroke.

Many patient interfaces are well known in the art. For instance, masks which provide a seal between the compressed air and the patient are common. These interfaces include nasal pillows with or without prongs which fit into the nares of the patient, nasal cannulas, nasal masks which fit over the patient's nose, nasal-oral masks that fit over the mouth and nose, and full face masks which fit over the patient's entire face. For such devices to be effective, two competing goals need to be balanced: comfort and functionality. Comfort may be enhanced by reducing the area of contact between the mask and the patient; or use of a soft, lightweight, flexible material. However, taken to an extreme, comfortable masks may prove to not function adequately. On the other hand, if comfort is not taken into account, even mechanically effective patient interfaces may have low patient compliance.

For purposes of description, the discussion herein is focused on patient interfaces and/or cannulas for use with human patients, it being understood that the present invention is not limited in scope only to use with human patients and can beneficially be used in various other contexts. For example, the present invention may also be used in the area of veterinary medicine where the "patients" are animals.

Different types of nasal interfaces are used to deliver gas, such as air or oxygen, to patients who need assistance to breathe properly, as discussed above, and/or to collect expired gas, such as carbon dioxide, from patients to monitor respiration. In some applications, a sidestream of the patient's exhaled breath flows through the interface to a gas analyzer to be analyzed. The results of this non-invasive analysis provide an indication of the patient's condition, such as the state of the patient's pulmonary perfusion, respiratory system, and/or metabolism.

Some nasal interfaces are perceived to not remain in position during use, and as a result are not comfortable to the patient. This may be due, in part, to differences between patients in the spacing between the patient's nostrils, the shape of the patient's nostrils, and/or the spacing between the patient's nose and mouth. It may also be due to differences in airflow from the two nostrils. It is desirable to provide an interface with improved comfort for the patient.

In addition, the nasal resistance between subjects can vary significantly. As such, the nasal airflow can often be quite asymmetric between the two nostrils. This can affect the efficiency of gas delivery, as the delivery will depend upon the nature of an obstruction in one or both nostrils, and how the gas is delivered. Gas that is allowed to escape from the system, i.e., not enter the patient's nostril upon exiting the cannula, decreases the efficiency of the system. A simple means to increase the amount of gas that is inhaled by the subject without wasting the gas is desired.

Many patient interfaces are configured to direct gas either directly into or directly out of the nasal cavity of the patient. While advantageous in some applications, it would be desirable to have a device which allows the gas to be directed into a particular direction to optimize the gas flow.

SUMMARY OF THE INVENTION

Accordingly, one aspect of the present invention provides a patient interface with improved stability and comfort to the patient, while also improving the efficiency with which gas is delivered to and/or received from the nostril(s) of the patient.

In an embodiment, a patient interface is provided. The patient interface includes a body portion that is configured to communicate with at least one fluid path, and at least one nostril interface that extends from the body portion. The nostril interface includes an insertion portion configured to be inserted into a nostril of a patient and to be in communication with the fluid path. The insertion portion includes at least one opening directed in a non-axial direction relative to the longitudinal axis of the insertion portion and configured to communicate fluid between the fluid path and the nostril. The patient interface also includes a seal portion that is constructed and arranged to provide a seal between the patient interface and the nostril.

In an embodiment, the patient interface includes a body portion that is configured to communicate with at least one fluid path, and at least one nostril interface that extends from the body portion. The nostril interface is configured to be inserted into a nostril of a patient and to be in communication with the at least one fluid path. The nostril interface includes a distal end having an opening and a sidewall extending between the distal end and the body portion. The patient interface also includes a cover at least partially covering the body portion and the nostril interface. The cover is configured to provide a seal between the patient interface and the nostril.

In an embodiment, a patient interface is provided. The interface includes a body portion that is configured to communicate with at least one fluid path, and a seal portion that extends from the body portion. The seal portion is constructed and arranged to provide a seal between the patient interface and a first nostril of a patient, and to provide a seal between the patient interface and a second nostril of the patient. The interface also includes a first nostril insertion portion that extends from the seal portion. The first nostril insertion portion includes at least one laterally directed opening and is constructed and arranged to be inserted into the first nostril of the patient. The interface also includes a second nostril insertion portion that is spaced from the first nostril insertion portion and extends from the seal portion. The second nostril insertion portion includes at least one laterally directed opening and is constructed and arranged to be inserted into the second nostril of the patient.

These and other aspects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
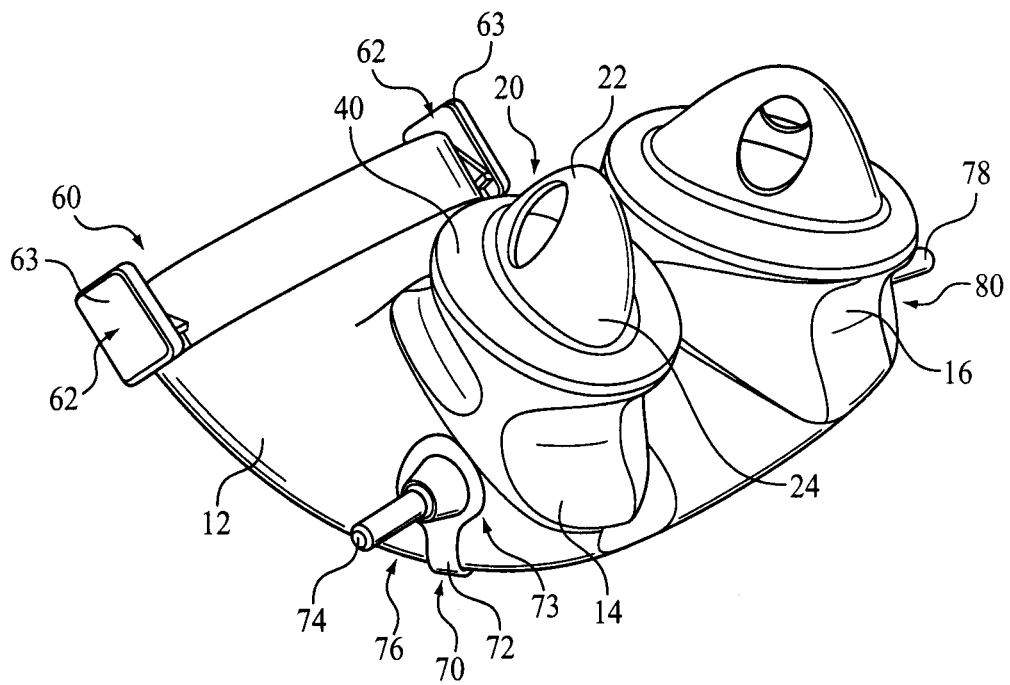
FIG. 1 is a perspective view of a patient interface according to an embodiment of the invention.

FIG. 1 illustrates a patient interface 10 according to an embodiment of the present invention. The patient interface 10 may be used as a gas delivery cannula or "appliance," or may be used as a gas sampling cannula or "appliance" or may be used as a combination gas sampling and delivery cannula or "appliance." As used herein, the term "patient interface" is intended to broadly refer to any device or structure that interfaces or cooperates with a patient, or has a portion thereof that interfaces or cooperates with a patient. The term "appliance" broadly refers to any device or structure that outputs a fluid, such as a gas, to and/or intakes a fluid, such as a gas, from a patient. The term "cannula" as used herein is one type of "appliance" and refers to a structure that has at least a portion thereof that protrudes into at least one nostril of a patient.

Figure 4:
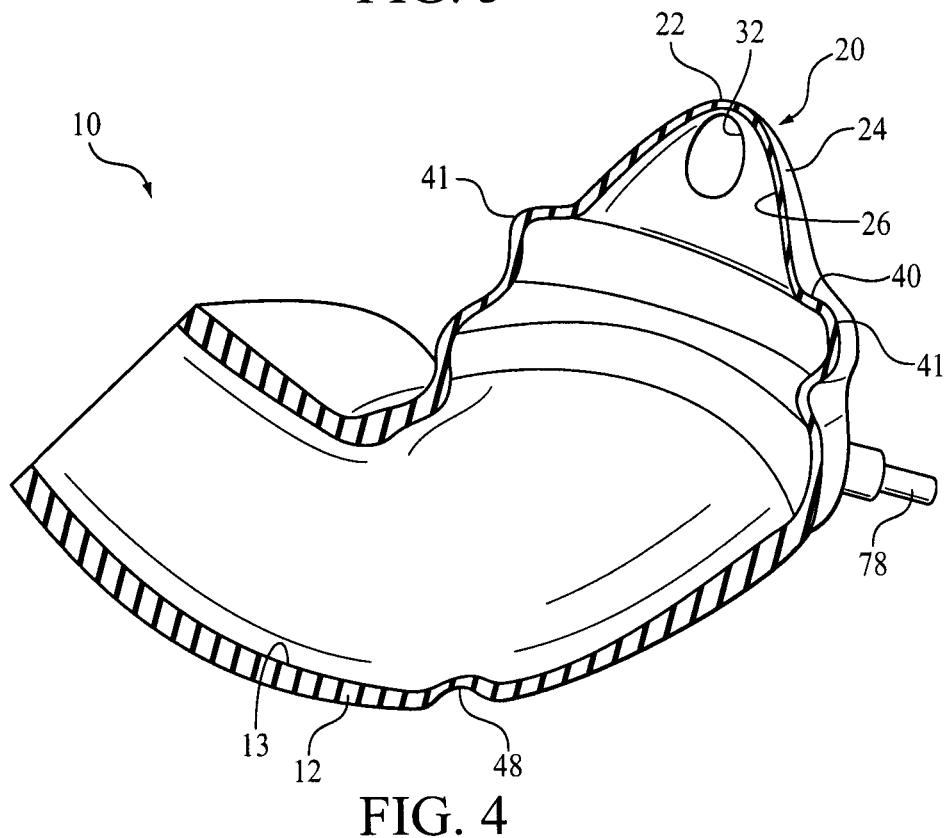
FIG. 4 is a cross-sectional view taken along line 4-4 in FIG. 3.

As shown in FIG. 1, the patient interface 10 includes a body portion 12, a first nostril interface 14 that extends from the body portion 12, and a second nostril interface 16 that extends from the body portion 12. The body portion 12 defines a fluid passageway 13, or conduit, which is best shown in FIG. 4. Because the first nostril interface 14 and the second nostril interface 16 are of substantially the same design, only the first nostril interface 14 will be discussed further, with the understanding that the second nostril interface 16 may include the same features, unless otherwise indicated herein.

Figure 2:
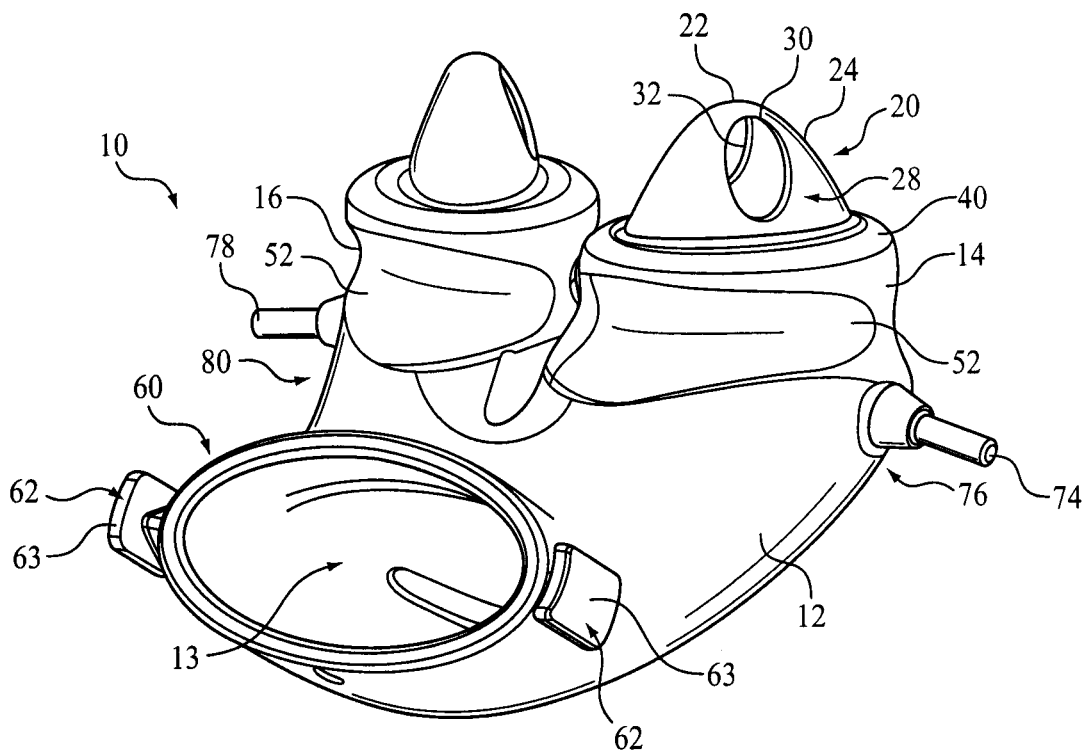
FIG. 2 is another perspective view of the patient interface of FIG. 1.

As shown in FIG. 2, and in greater detail in FIG. 4, the nostril interface 14 includes an insertion portion 20 that is configured to be inserted into a nostril of a patient. As illustrated, the insertion portion 20 has a distal end 22 and a sidewall 24 that extends from the distal end 22 towards the body portion 12. In the illustrated embodiment, the sidewall 24 is generally conical in shape, and the distal end 22 is shaped like a rounded tip of a cone. Of course, other shapes of the sidewall are contemplated. For example, the sidewall may be of a tulip shape in which a center portion of the sidewall bulges outwardly, as compared to the tip and base of the sidewall, or the sidewall may be more cylindrical in shape. The illustrated embodiment is not intended to be limiting in any way.

The nostril interface 14 defines a fluid passageway 26, or conduit, best shown in FIG. 4, that is configured to be in communication with the fluid passageway 13 in the body portion 12. The fluid passageway 13 in the body portion 12 is configured to be in communication with a fluid path, as discussed in greater detail below, so that the fluid may pass through the passageway 13 and into the passageway 26, or vice-versa. The passageways 13, 26 may be suitably sized so that the a gas, such as air or oxygen, may be delivered to the patient's nostril at an appropriate pressure for comfortable inhalation, and/or so that a gas, such as carbon dioxide, being exhaled by the patient may flow out of the patient interface 10 such that little or no resistance is felt by the patient upon exhalation.

Figure 3:
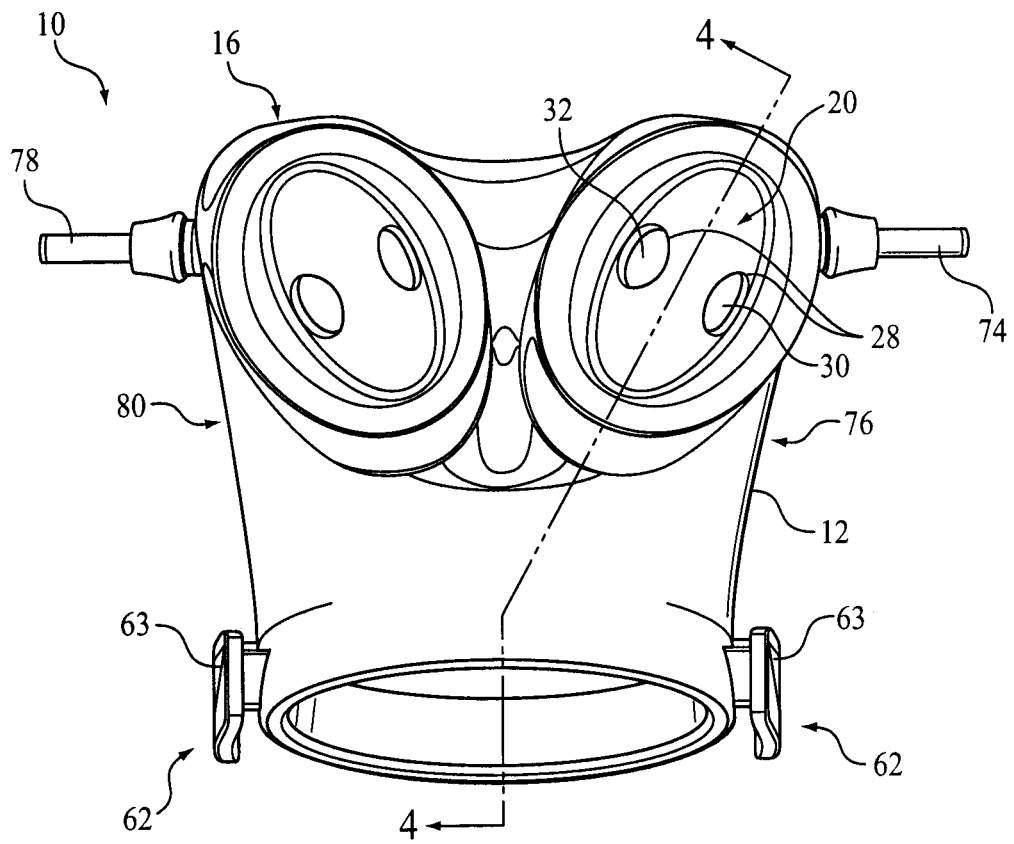
FIG. 3 is a top view of the patient interface of FIG. 1.

As illustrated in FIG. 3, the sidewall 24 of the nostril interface 14 includes at least one laterally directed opening 28 that is configured to communicate fluid between the fluid path and the nostril via the passageways 13, 26. In the embodiment illustrated in FIG. 3, the insertion portion 20 includes a plurality of laterally directed openings, including a first opening 30 and a second opening 32 that are located in opposite sides of the insertion portion 20. This configuration allows fluid to be communicated between the fluid path and portions of the nostril that are located on opposite sides, e.g. left and right, of the insertion portion 20. When fluid is supplied to the nostril through the laterally directed openings, a more diffused air pattern may be created, as compared to a nostril interface that includes a single opening on a distal end of the nostril interface, which may decrease the dry sensation that is felt by the patient.

Figure 5:
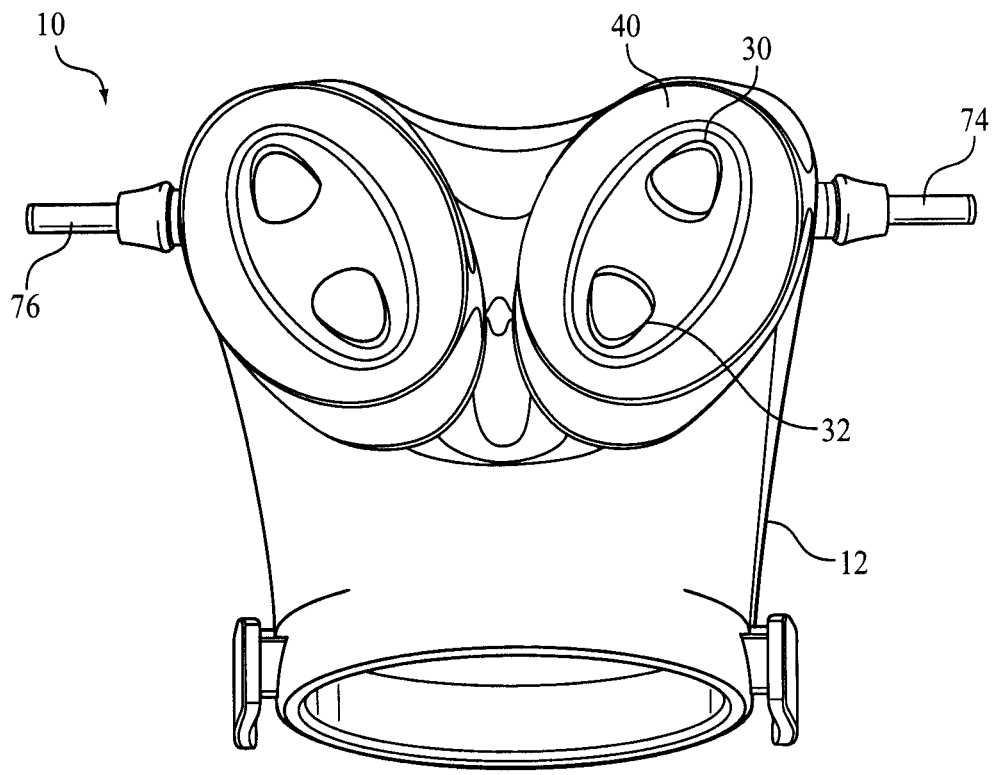
FIG. 5 is a top view of a patient interface according to another embodiment of the invention.

The locations of the first opening 30 and the second opening 32 may vary, and are not limited to the configuration illustrated in FIG. 3. For example, the first opening 30 and the second opening 32 may be located on front and back sides of the insertion portion 20, as shown in FIG. 5. In the embodiments illustrated in FIGS. 3 and 5, the first opening 30 and the second opening 32 are located about 180° from each other around the circumference of the sidewall 24 of the insertion portion 20. Of course, the first opening 30 and the second opening 32 may be located at different locations around the circumference of the sidewall 24 of the insertion portion 20. The illustrated embodiments are intended to generally illustrate two of many possible configurations, and not intended to be limiting in any way.

Figure 6:
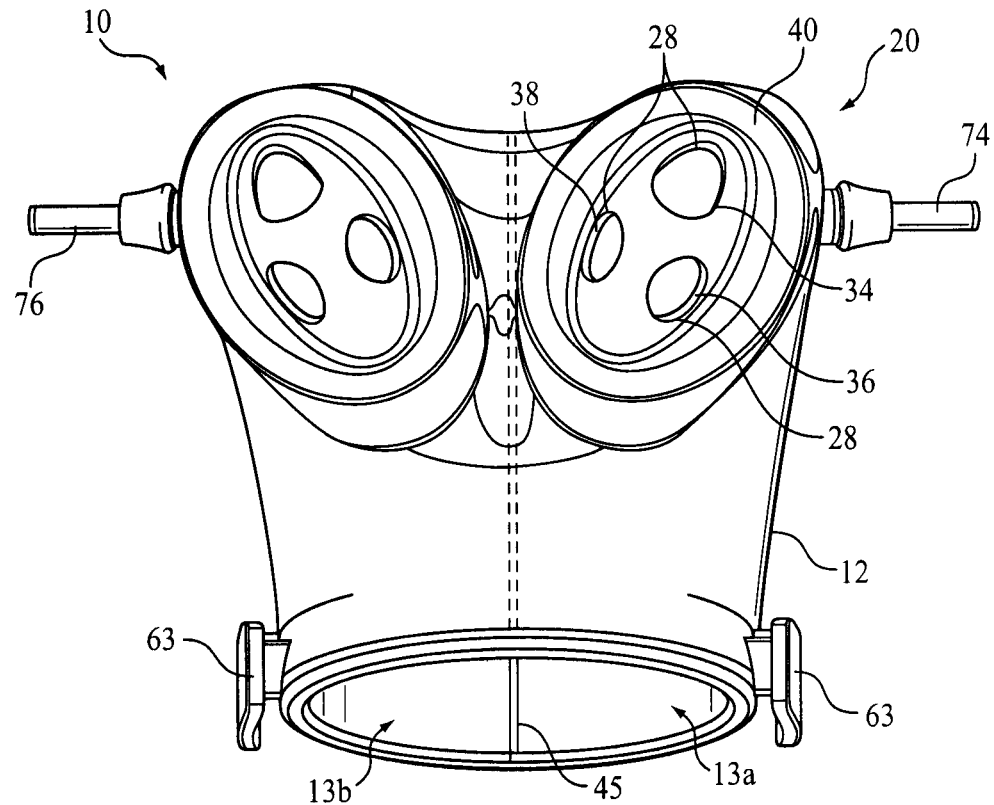
FIG. 6 is a top view of a patient interface according to another embodiment of the invention.

As illustrated in the embodiment of FIG. 6, the insertion portion 20 may include a first opening 34, a second opening 36, and a third opening 38 that are equally spaced from each other around the circumference of the sidewall 24 of the insertion portion 20. This configuration allows fluid to be communicated between the fluid path and three portions of the nostril that surround the insertion portion 20. Of course, any number of openings 28 may be used to communicate the fluid between the fluid path and the nostril. The openings 28 may be sized so that the flow of the fluid is not impeded (or only slightly impeded) and the backpressure within the interface 10 is within acceptable levels to ensure a comfortable feel for the patient. The size and shape of each opening 28 may differ. While the shape of the openings are shown as elliptical, they may have a variety of other cross-sectional geometries. In addition, a plurality of openings are shown; however, a single opening may also be used. One unique aspect of the invention is that the opening is configured to direct fluid flow in a direction other than along the longitudinal axis of the nasal passage and upward into the sphenoidal sinuses which may cause discomfort to the patient. Instead, the fluid flow may be directed laterally, to the front, to the back, or in any other non-longitudinal direction optimized to enhance patient comfort. The illustrated embodiments are not intended to be limiting in any way.

As shown in FIG. 4, the nostril interface 14 also includes a seal portion 40 that is constructed and arranged to provide a seal between the patient interface 10 and the nostril. In the illustrated embodiment, the seal portion 40 is integral with the insertion portion 20, i.e., the seal portion 40 is formed with the insertion portion 20 and extends from the insertion portion 20. The seal portion 40 extends radially outwardly from the insertion portion 20 and has a surface 41 that is configured to engage a lower exterior surface and/or an interior portion of the nostril so that no or essentially no fluid passes between the seal portion 40 and the nostril. This should force the fluid that is being supplied through the passageways 13, 26, out of the openings 28, and into the nostril so that it may be inhaled by the patient, without substantial leaking out of the patient's nostril and into the surrounding atmosphere. This is because the seal portion 40 should prevent or substantially prevent the fluid from flowing between the patient interface 10 and the nostril. Similarly, if the patient interface 10 is being used to sample fluid being exhaled by the patient, the fluid should be forced into the openings 28 to escape the nostril, because the seal portion 40 should prevent or substantially prevent the fluid from passing between the nostril and the patient interface 10. Such as arrangement may provide a more efficient design, as less gas will be leaked to the surrounding environment.

Figure 7:
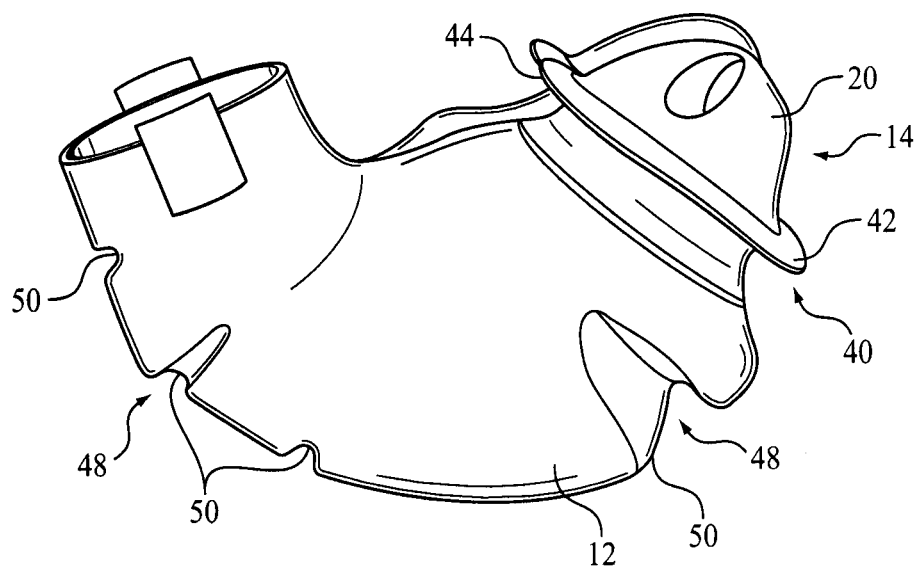
FIG. 7 is a side view of a patent interface according to another embodiment of the invention.
Figure 8:
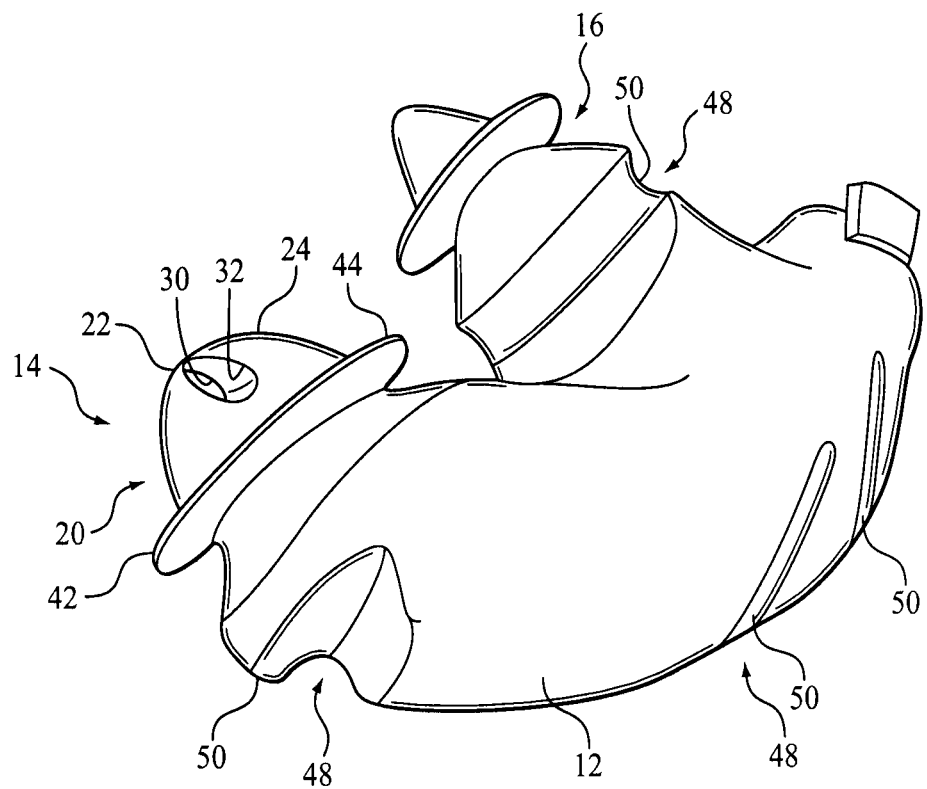
FIG. 8 is a bottom, right perspective view of the patient interface of FIG. 7.

As illustrated in the embodiment of FIGS. 7 and 8, the seal portion 40 may include a flange 42 that circumferentially surrounds the insertion portion 20 and is configured to engage an interior surface and/or an exterior surface of the nostril of the patient when the insertion portion 20 is inserted into the nostril. In an embodiment, the flange 42 is integral with the insertion portion 20, and is configured to be inflated (e.g. like a balloon) by the fluid being communicated between the fluid path and the nostril (i.e., oxygen or an air supply). For example, the flange 42 may include a thin flexible membrane 44 that is configured to be inflated with fluid that is being supplied to the patient via the patient interface 10. The thin membrane 44 may be a thinned portion of the insertion portion 20. By providing a thin, inflatable membrane 44, the flange 42 may conform with the opening of the patient's nostril so as to provide a seal, and also provide a cushion between the nostril interface 14 and the nostril, which may provide additional comfort to the patient. In another embodiment, the flange 42 may not be inflatable, but may be still flexible so as to conform to the opening of the nostril and also provide a comfortable seal between the nostril interface 14 and the nostril.

In an embodiment, illustrated in FIG. 6, the body portion 12 may include a separator 45 that is configured to separate the passageway 13 in the body portion into two passageways 13a, 13b that communicate with the passageway 26 in the first nostril interface 14 and the passageway in the second nostril interface 16, respectively. In this embodiment, the first nostril interface 14 is constructed and arranged to deliver gas, such as air or oxygen, from a first fluid path to one nostril of the patient, and the second nostril interface 16 is configured to receive sampled fluid expired from the patient through the other nostril and deliver the expired fluid to a second fluid path. Of course, depending on how the fluid paths are connected to the body portion 12, oxygen may be delivered to the patient through the second nostril interface 16, and fluid expired from the patient may enter the first nostril interface 14 and be communicated through the body portion 12 to one of the fluid paths The body portion 12 and the first and second nostril interfaces 14, 16 may be formed from the same material. Preferably, the body portion 12 and the first and second nostril interfaces 14, 16 are integrally molded from a soft, flexible material, such as an elastomeric material, that provides a comfortable fit with the patient. As shown in greater detail in FIGS. 7 and 8, the body portion 12 may include at least one flexible section 48 that is constructed and arranged to allow the body portion 12 to be adjusted. Adjustments within the body portion 12 may help to insure that the insertion portions 20 of the nostril interfaces 14, 16 are properly positioned in the patient's nostrils, and the body portion 12 rests comfortably above the patient's upper lip. The flexible section 48 may include a recess or groove 50 that is configured to allow one section of the body portion 12 to pivot relative to another section of the body portion 12. The flexible section 48 may include a malleable material that allows the one section to remain in place relative to the other section once the one section has been pivoted relative to the other section. In another embodiment, the flexible section 48 may be a bellows-type structure, such as those commonly found in plastic drinking straws.

Similarly, the nostril interfaces 14, 16 may each include a flexible section 52, as shown in FIG. 2 that allows for adjustment of each nostril interface 14, 16 relative to the body portion 12. A malleable material or bellows-type structure may be used in the flexible sections 52 so that once an adjustment has been made between the nostril interface and the body portion, the adjustment may hold its configuration until a further adjustment is made.

Figure 18:
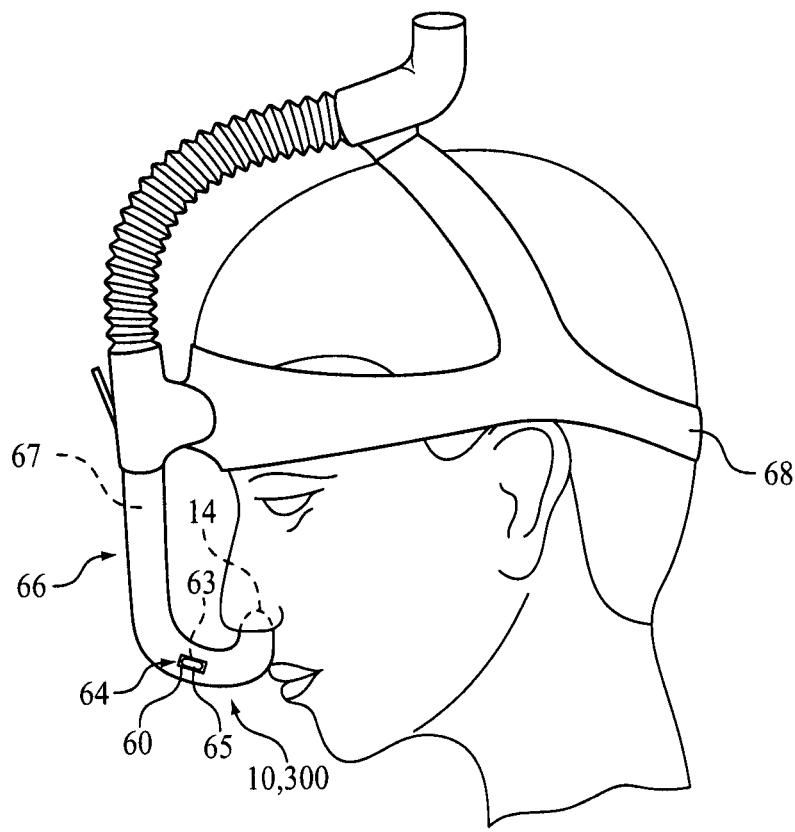
FIG. 18 is a side view of the patient interface of FIG. 1 as it is mounted to a patient according to an embodiment of the invention.

As shown in FIG. 1, the interface 10 also includes a fluid path interface 60 that extends from the body portion 12. The fluid path interface 60 is configured to connect the patient interface 10 to a conduit 66 that defines at least one fluid path 67, as shown in FIG. 18. In the illustrated embodiment, the fluid path interface 60 includes a locking structure 62 that is configured to lock with a portion 64 of the conduit 66 that defines the fluid path 67. Specifically, the locking structure 62 includes a pair of tabs 63 that are located on opposite sides of one end of the body portion, as shown in FIGS. 1-3. Each tab 63 is configured to be received by a corresponding sleeve 65 located on opposite sides of the conduit 66. To lock the patient interface 10 to the conduit 66, the tabs 63 are slidingly received by the corresponding sleeves 65. Friction between the tabs 63 and the sleeves 65 holds the tabs 63 within the sleeves 65 until sufficient force is used to pull the tabs 63 out of the sleeves. Of course, other locking arrangements between the patient interface 10 and the conduit 66 may be provided. The illustrated embodiments are not intended to be limiting in any way.

As shown in FIG. 18, the conduit 66 may be held in place relative to the patient with head gear 68 that is constructed and arranged to route the conduit 66 up and over the patient's head. By supporting the conduit 66 with the illustrated head gear 68, movement of the patient's head does not disturb the positioning of the conduit 66 relative to the patient's nose, thereby allowing the patient interface 10 to stay in place relative to the patient's nostrils. The illustrated embodiment is intended to illustrate one possible way to hold the patient interface 10 in place relative to the patient's nose, and is not intended to be limiting in any way.

In an embodiment, the interface 10 may include an adjustor 70, illustrated in FIG. 1, that is configured to adjust the body portion 12 so that an orientation, including position, of the first nostril interface 14 may be adjusted relative to the second nostril interface 16. The adjustor 70 includes a flexible adjustment band 72 that is configured to attach to the body portion 12 on opposite sides thereof, as explained in further detail below. Because the spacing between the nostrils and/or the shape of the nostrils of different patients is different, the orientation of, including the distance between, the nostril interfaces 14, 16 can be altered based upon the particular patient's nostril spacing.

In the embodiment illustrated in FIG. 1, the adjustor 70 also includes a first extension 74 that extends from one side 76 of the body portion 12 and a second extension 78 that extends from an opposite side 80 of the body portion 12. The first extension 74 and the second extension 78 are configured to be connected with the adjustment band 72 so as to hold the adjustment band in tension, which may cause the body portion 12 to flex, thereby adjusting the orientation of one nostril interface relative to the other nostril interface. In the illustrated embodiment, the adjustment band 72 includes a loop 73 at each end thereof that is configured to engage the first and second extensions 74, 78 so that the adjustment band 72 may be held in tension between the extensions 74, 78. If further adjustment is needed, another adjustment band having a different length and/or stretch characteristic may be used instead of or in addition to the adjustment band. For example, if the nostril interfaces 14, 16 are to be positioned closer together, a shorter adjustment band 72 may be used in comparison with the one illustrated. The adjustment band 72 may be made from any suitable flexible material, including but not limited to a metal such as aluminum or a polymeric material. The configuration and operation of adjustors are fully described in U.S. Patent Application Publication No. 2005-0076913. The contents of which are hereby incorporated by reference in their entirety.

As indicated above, the patient interface 10 illustrated in FIGS. 1-8 and 18 may be used as a nasal gas delivery device. In some embodiments, the patient interface may be used as a nasal gas sampling device. Depending on how the fluid paths and internal passageways 13, 26 are configured, the patient interface 10 may be configured to provide gas sampling from one nostril interface and gas delivery to the other nostril interface. It is also contemplated that the nostril interfaces may be configured to provide gas sampling and/or gas delivery to both nostrils with appropriate passageways defined therein, as can be appreciated by those skilled in the art. The above-described and illustrated embodiments are not intended to be limiting in any way.

Figure 9:
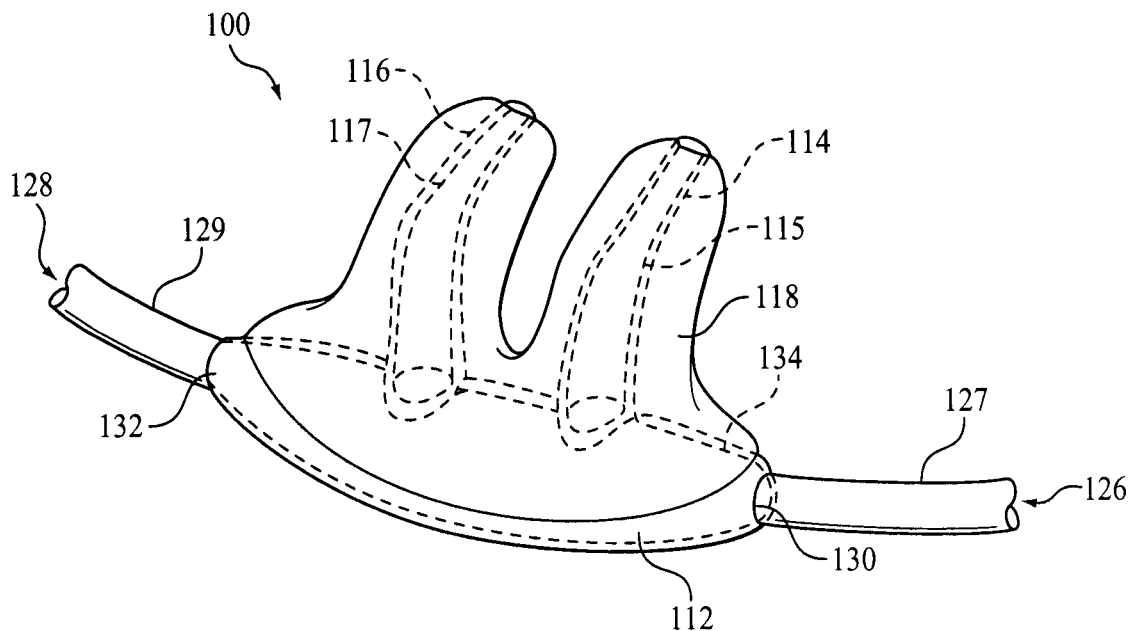
FIG. 9 is a rear perspective view of a patient interface according to another embodiment of the invention.
Figure 10:
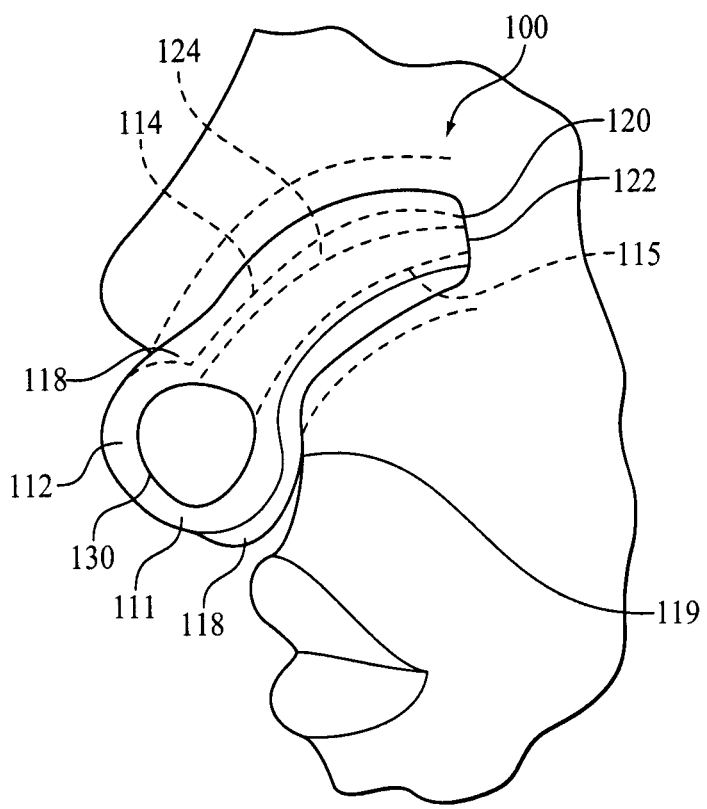
FIG. 10 is a schematic view of a nostril interface of the patient interface of FIG. 9, as inserted into a nostril of a patient.

FIG. 9 illustrates another embodiment of a patient interface 100 that includes a body portion 112 that is configured to communicate with at least one fluid path. The interface 100 also includes a first generally tubular nostril interface 114 that projects from the body portion 112, and a second generally tubular nostril interface 116 that also projects from the body portion 112 in a generally parallel orientation relative to the first nostril interface 114. As seen in FIGS. 9 and 10 the interfaces may be angled to conform with the shape of the patient's nasal passage. The body portion 112, nostril interface 114, and nostril interface 116 may, in one embodiment, all be in fluid communication with one another.

Although there are two nostril interfaces 114, 116 in the illustrated embodiment, it is contemplated that in some embodiments, only one nostril interface may be provided. Because the first nostril interface 114 and the second nostril interface 116 may generally be of the same design, only the first nostril interface 114 will be discussed in further detail, with the understanding that the second nostril interface 116 includes the same features, unless otherwise indicated herein. The nostril interface 114 is configured to be inserted into a nostril of a patient and to be in communication with the fluid path.

The interface 100, in one embodiment, includes a cover 118 that at least partially surrounds the body portion 112 and the nostril interfaces 114, 116. In the illustrated embodiment, the cover 118 only partially surrounds the body portion 112, thereby leaving a portion 111 of the outside surface of the body portion 112 exposed, as shown in FIG. 10. However, the portion 111 of the body portion 112 that is exposed is not intended to come into direct contact with the patient, and only the cover 118 should come into contact with the patient's skin, as shown in FIG. 10. As discussed in further detail below, the cover 118 is configured to provide a seal between the nostril interfaces 114, 116 and the nostrils so that fluid can only enter or exit the nostrils through the nostril interfaces 114, 116. Cover 118 and/or interfaces 114, 116 may be shaped to conform with the shape of the patient's nasal passage.

Figure 12:
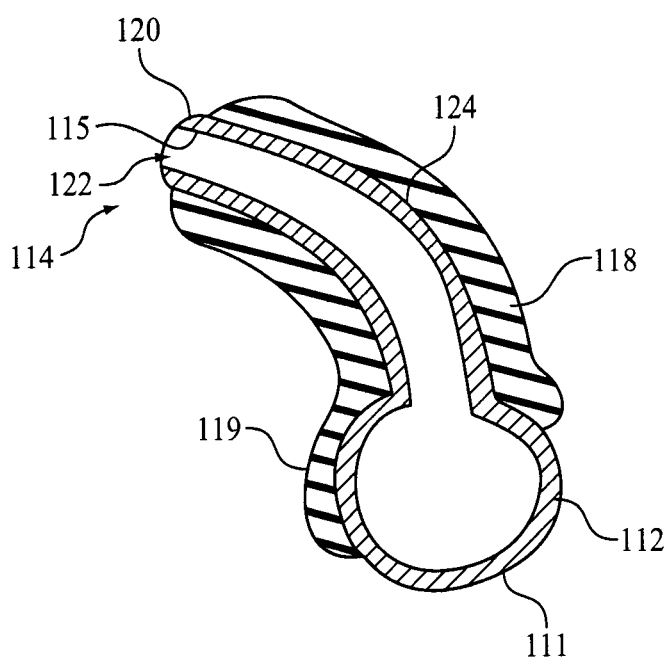
FIG. 12 is a cross-sectional view of the nostril interface of the patient interface of FIG. 1.

As shown in FIG. 12, the nostril interface 114 includes a distal end 120 that includes an opening 122, and a sidewall 124 that extends between the distal end 120 and the body portion 112. The sidewall 124 is curved so as to substantially conform to the shape of the nostril of the patient so that the opening 122 in the distal end 120 is substantially centered in the nostril, as shown in FIG. 10. Alternatively, one or more holes may be formed about the circumference of interfaces 114, 116, and/or cover 118 to direct the fluid flow in a direction other than along the longitudinal axis of the nasal passage of the patient and into the patient's sphenoidal sinuses. For instance, the fluid flow may be directed towards the front, towards the back, laterally, or in any other direction.

In an embodiment, the body portion 112 and the nostril interfaces 114, 116 are integrally formed, e.g., molded, from the same material having a hardness of about 70 durometers shore A, such as silicone. As described in more detail below, cover 118 may be formed of a comparatively softer material to enhance comfort to the patient. In fact, it is contemplated that as a more rigid material is utilized for interfaces 114, 116 to provide adequate structural rigidity a softer material may be used for the cover 118 to enhance the comfort provided to the user. Of course, one of ordinary skill in the art can best appreciate that other materials may be used and the examples given should not be considered to be limiting in any way.

The body portion 112 is constructed and arranged to be operatively connected to one or more fluid paths. In the illustrated embodiment, a first fluid path 126 and a second fluid path 128 are provided by tubing 127 and 129, respectively. The term "tubing" as used herein is intended to refer to a flexible tube. Of course any suitable structure for transporting fluids may be configured to define the fluid paths. In the illustrated embodiment, the body portion 112 has a pair of tubing connecting portions 130, 132 for interfacing and/or connecting with fluid path 126 and fluid path 128, respectively.

In one embodiment, the connecting portions 130, 132 comprise respective orifices in the body portion 112, which orifices each have an inner diameter configured to form a friction fit with the outer diameter of an associated one of the tubes 127, 129. Other mechanisms for forming connections between the body portion 112 and the tubing 127, 129 or fluid paths 126, 128 are possible. For example, the connecting portions 130, 132 on the body portion 112 may be in the form of projections, each containing a passage therein and having an outer surface with an outer diameter configured to form a friction fit with the inner diameter of an associated one of the tubes, etc. In other embodiments, the connection may be achieved by an adhesive or other joining structure. In another embodiment, the tubing and the body portion may be integrally formed. The disclosed embodiments are not intended to be limiting in any way.

Figure 19:
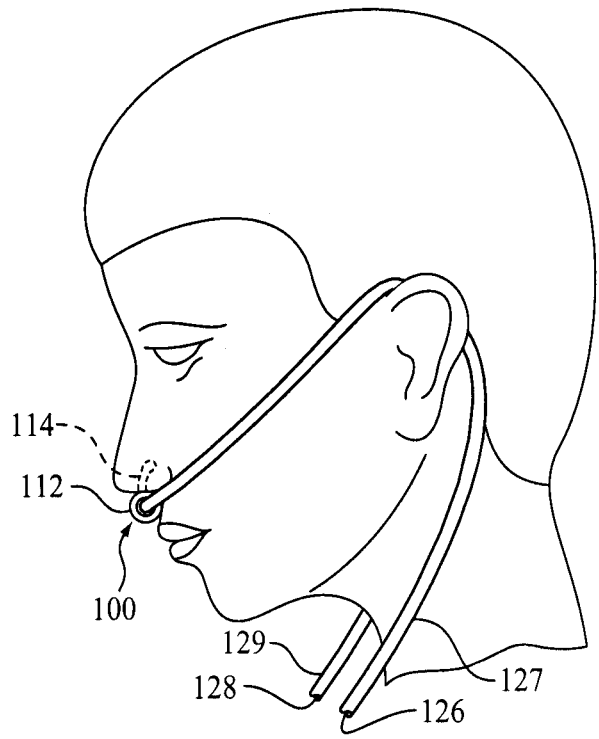
FIG. 19 is a side view of the patient interface of FIG. 13 as it is mounted to a patient according to an embodiment of the invention.

As shown in FIG. 19, the tubing 127, 129 of the patient interface 100 may be configured to extend from the body portion 112 and at least partially around each ear of the patient to hold the body portion 112 in a generally stable position relative to the nose of the patient. The nostril interfaces 114 and 116 are configured to be inserted into an associated nostril of a patient and so that the respective openings 122 are arranged to be in communication with the associated fluid paths 126 and 128, respectively. One of ordinary skill in the art will appreciate that there are many ways to hold the patient interface 100 in place relative to the patient's nose. The illustrated embodiment is not intended to be limiting in any way, and is merely provided as an example of how the patient interface 100 may be mounted to the patient.

Figure 11:
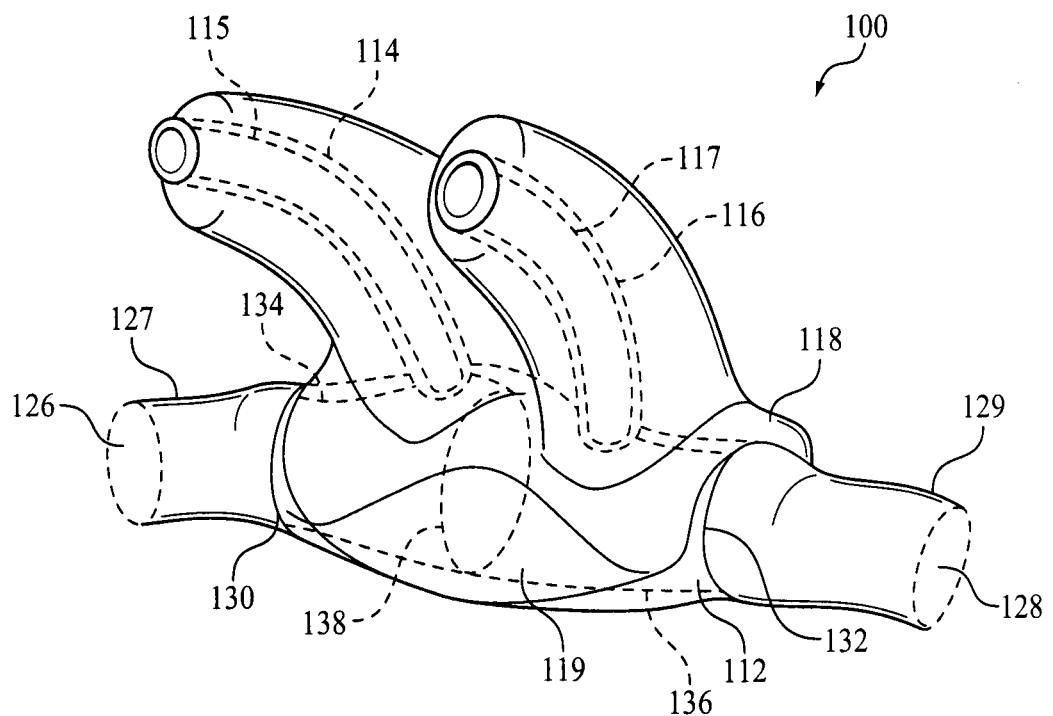
FIG. 11 is a perspective view of the patient interface of FIG. 9.

As shown in FIG. 11, communication between the nostril interface 114 and the orifice of connecting portion 130 is provided by an internal conduit 134 within the body portion 112 and an internal conduit or passageway 115 within the nostril interface 114. Similarly, an internal conduit 136 communicates an internal conduit or passageway 117 within the nostril interface 116 with the connecting portion 132, as known in the art. This allows the fluid paths 126 and 128 to be in fluid communication with the nostrils so that fluids may either be received from the patient and/or supplied to the patient.

In one embodiment, nostril interface 114, connecting portion 130, and fluid path 126 may be configured to supply a fluid (e.g., gas) that includes oxygen (e.g., air or essentially pure oxygen) to the patient from a suitable fluid supply, and nostril interface 116, connecting portion 132, and fluid path 128 may be configured to receive a fluid that includes gas (e.g., carbon dioxide) that has been expired from the patient. In such an embodiment, the fluid path 128 communicates the fluid to a suitable device, such as a gas analyzer, so that the concentration of the carbon dioxide in the expired fluid and/or rate of flow of the expired fluid may be monitored over time. In such an embodiment, an internal wall structure 138, shown in FIG. 11, seals the internal conduit 134 communicating with the internal passageway 115 of nostril interface 114 from the internal conduit 136 communicating with the internal passageway 117 of nostril interface 116. In one embodiment, this internal wall structure may be formed in accordance with the teachings of U.S. Pat. No. 5,335,656, which is hereby incorporated by reference in its entirety.

It should also be appreciated that while the fluid path 126, connecting portion 130, and internal passageway 115 of nostril interface 114 are mentioned above in one embodiment as being used for gas delivery, while fluid path 128, connecting portion 132, and internal passageway 117 of nostril interface 116 are mentioned as being used for gas sampling, these may be reversed depending on which nostril (left or right) is preferred for gas (e.g., carbon dioxide) sampling versus gas (e.g., oxygen) delivery.

In one embodiment, the internal passageways 115, 117 of the nostril interfaces 114, 116 and associated fluid paths 126, 128 all deliver air or oxygen to the patient. In another embodiment, the internal passageways 115, 117 of the nostril interfaces 114, 116 and associated fluid paths 128, 130 all receive a fluid that includes carbon dioxide from the patient. In either of these embodiments, the internal wall structure 138 may not be necessary, and the internal conduits 134, 136 may be a single internal conduit.

The cover 118 may include a soft material having a hardness of less than about 20 durometers Shore 000. In an embodiment, the material may comprise an elastomeric material. In another embodiment, the cover 118 may include a material having a hardness of about 3 to about 5 durometers Shore A, such as silicone rubber. In another embodiment, the cover 118 includes a gel material that may be a thermoset or thermoplastic material. Such soft materials may provide comfort to the patient, as the cover is in contact with the patient's skin, both inside the nostril and at an area between the patient's nostrils and upper lip.

The cover 118 is configured to be conformable with the inside surfaces of the patient's nostrils so that when the nostril interfaces 114, 116 and cover 118 are inserted into the patient's nostrils, as shown in FIG. 10, the cover 118 provides a seal between the nostril interfaces 114, 116 and their respective nostrils, without exerting too much pressure on the patient that may create discomfort to the patient. The cover 118 includes a portion 119 that is configured to extend substantially around one side of the body portion 112 and is also configured to engage an area of the patient's skin between the nostril and the upper lip, as shown in FIG. 10.

Figure 13:
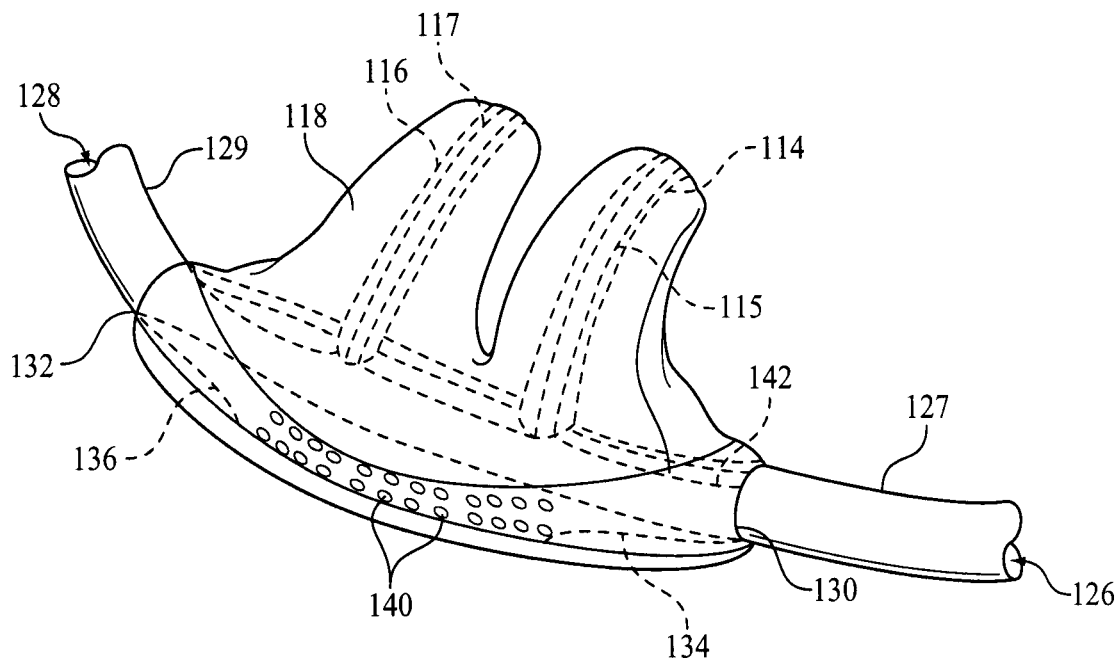
FIG. 13 is a perspective view of a patient interface according to another embodiment of the invention.
Figure 14:
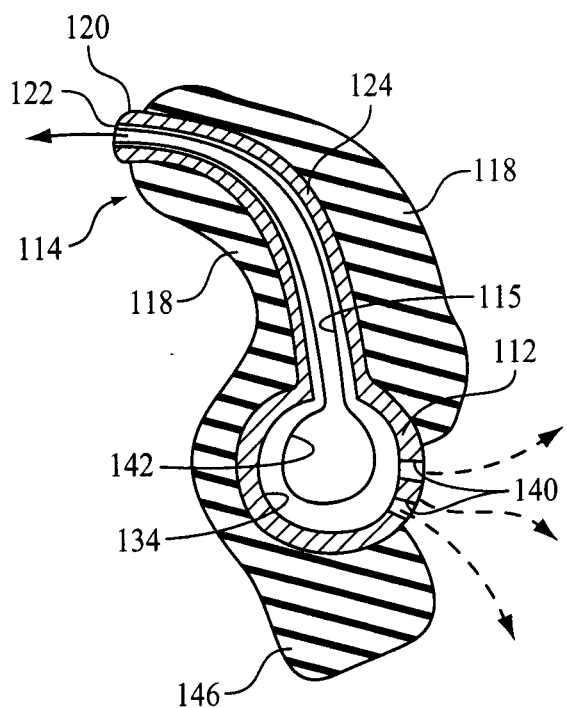
FIG. 14 is a cross-sectional view of a nostril interface of the patient interface of FIG. 13.

As shown in FIGS. 13 and 14, the body portion 112 may include a plurality of small openings 140 that are configured to allow fluid that is expired by the patient through one or both of the nostril interfaces 114, 116 to flow from the body portion 112 and directly to atmosphere, rather than through one of the fluid paths 126, 128. Such a configuration would allow both fluid paths 126, 128 to deliver air or oxygen to the nostril interfaces 114, 116, and also allow carbon dioxide being expired by the patient to exit the patient interface 100.

In the embodiment illustrated in FIGS. 13 and 14, the body portion 112 includes an internal passageway 142 that is surrounded by the internal conduits 134, 136 and is in fluid communication with the fluid paths 126, 128 via the connecting portions 130, 132 of the body portion 112. Similarly, the internal passageways 115, 117 of the nostril interfaces 114, 116 may be in fluid communication with the internal passageway 142 of the body portion 112. Such a configuration may substantially or completely prevent the gas being delivered by the fluid paths 126, 128 to the internal passageways 115, 117 of the nostril interfaces 114, 116 from escaping through the openings 140 in the body portion 112. The internal conduits 134, 136 and passageways 115, 117 may be configured so that the proper back pressures and flow rates may be provided so that the gas flows into the nostrils and carbon dioxide flows out of the nostrils in a controlled manner. The illustrated embodiment is not intended to be limiting in any way.

As illustrated in FIG. 14, the cover 118 may be configured to more completely surround the body portion 112 such that only the area of the body portion 112 where the openings 140 are located is not covered. Specifically, in the illustrated embodiment, the cover 118 includes an extension 146 that extends downwardly from the body portion 112. The extension 146 may be configured to engage an area of the patient's face just above the upper lip, as well as the upper lip, without causing discomfort to the patient. Such an extension 146 may provide further support for the patient interface 100 as the fluid containing carbon dioxide is being exhaled by the patient, so as to counter the force created on the body portion 112 by the fluid flowing out of the openings 140.

Figure 15:
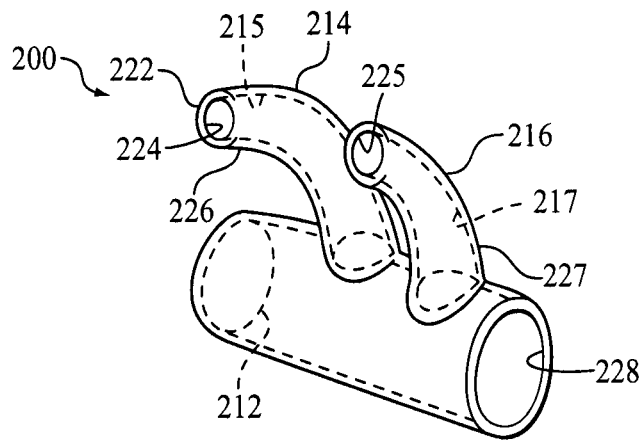
FIG. 15 is a perspective view of a body portion and nostril interfaces of a patient interface according to another embodiment of the invention.
Figure 16:
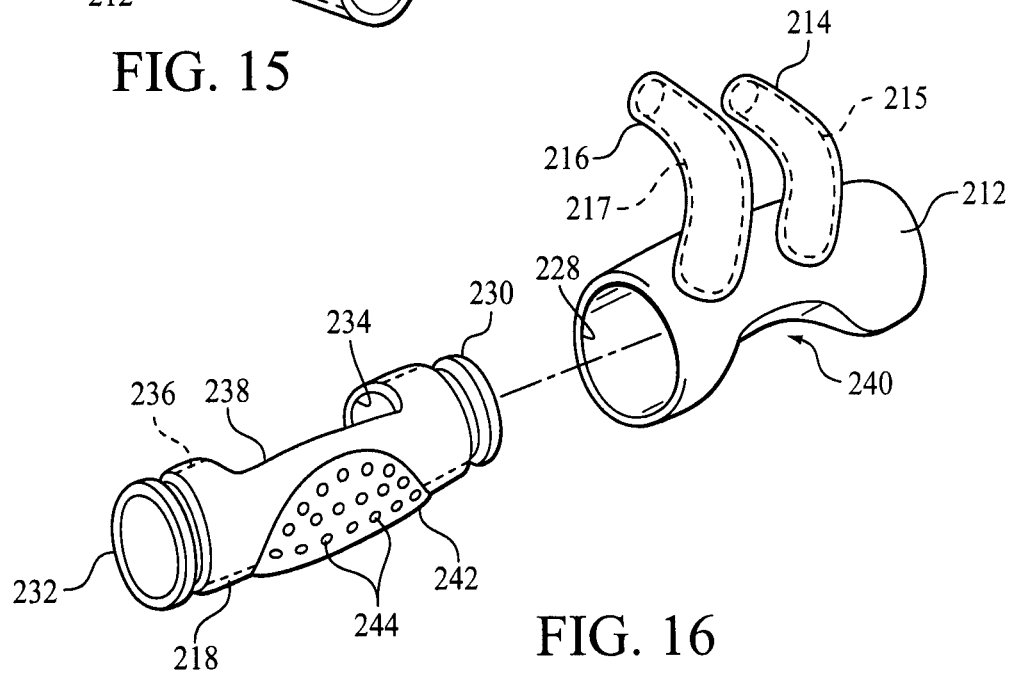
FIG. 16 is a perspective view of the body portion and nostril interfaces of FIG. 15, and a coupling of the patient interface according to an embodiment of the invention.
Figure 17:
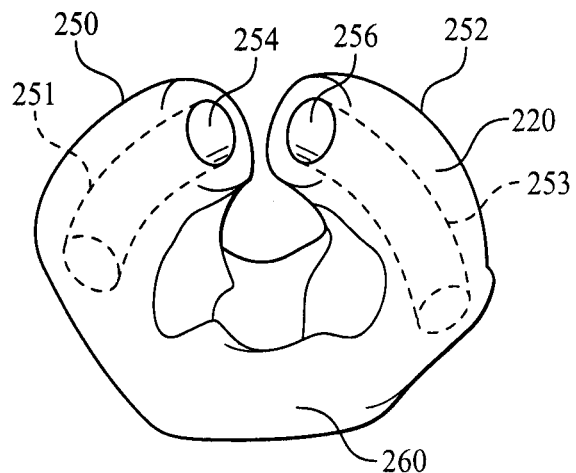
FIG. 17 is a perspective view of a cover for the body portion and nostril interfaces of FIG. 15.

FIGS. 15-17 illustrate another embodiment of a patient interface 200 according to the present invention. The patient interface 200 of this embodiment includes a body portion 212 having a first generally tubular nostril interface 214 that projects from the body portion 212, and a second generally tubular nostril interface 216 that also generally projects from the body portion 212 in a substantially parallel relation to the first nostril interface 114. The patient interface 200 also includes a coupling 218, illustrated in FIG. 16, and a cover 220, illustrated in FIG. 17.

Although there are two nostril interfaces 214, 216 in the illustrated embodiment, it is contemplated that in some embodiments, only one nostril interface may be provided. Because the first nostril interface 214 and the second nostril interface 216 are of substantially the same design, only the first nostril interface 214 will be discussed further, with the understanding that the second nostril interface 216 includes the same features, unless otherwise indicated herein. The nostril interface 214 is configured to be inserted into a nostril of a patient and to be in communication with the fluid path.

As shown in FIG. 15, the nostril interface 214 includes a distal end 222 that includes an opening 224, and a sidewall 226 that extends between the distal end 222 and the body portion 212. The sidewall 226 is curved so as to substantially conform with the shape of the nostril of the patient so that the opening 224 in the distal end 222 is substantially centered in the nostril, similar to the embodiment shown in FIG. 10. However, opening 224 may also be extend to the front, to the rear, or laterally from interfaces 214, 216. The sidewall 226 defines an internal passageway 215, or conduit, that allows fluid to flow between the opening 224 and the body portion 212. Similarly, the nostril interface 216 has a sidewall 227 that defines an internal passageway 217, or conduit, that allows fluid to flow between an opening 225 located at a distal end of the interface 216 and the body portion 212. In an embodiment, the body portion 212 and the nostril interfaces 214, 216 are integrally formed, e.g., molded, from the same material having a hardness of about 70 durometers shore A, such as silicone. Of course, other materials may be used and the example given should not be considered to be limiting in any way.

The coupling 218 (see FIG. 16) is constructed and arranged to couple each fluid path to the body portion 212. The coupling 218 is configured to be received by an internal passageway 228 of the body portion 212 and form a frictional fit with the internal passageway 228 of the body portion 212. Although not shown, in this embodiment, the fluid paths may be provided by tubing in a similar manner that the first and second fluid paths 126, 128 are provided by tubing 127, 129, as described above.

The coupling 218 includes a first connecting portion 230 and a second connecting portion 232. In one embodiment, the connecting portions 230, 232 comprise respective orifices that each have an outer diameter configured to form a friction fit with the inner diameter of an associated one of the tubes. A pair of clamps (not shown) may be used to clamp the respective tube onto each connecting portion 230, 232 to further secure the connection between the tubes and the patient interface 200.

Other mechanisms for forming connections between the coupling 218 and the tubing or fluid paths are possible. For example, the connecting portions 230, 232 on the coupling 218 may have inner diameters that are configured to form a frictional fit with the outer diameter of an associated one of the tubes, etc. In other embodiments, the connection may be achieved by an adhesive or other joining structure. In another embodiment, the tubing and the coupling 218 may be integrally formed. The disclosed embodiments are not intended to be limiting in any way.

Communication between the internal passageway 215 of the nostril interface 214 and the orifice of connecting portion 230 may be provided by an internal conduit 234 within the coupling 218. Similarly, an internal conduit 236 may communicate the internal passageway 217 of the second nostril interface 216 with the orifice of the connecting portion 232. This allows the associated fluid paths to be in fluid communication with the nostrils so that fluids may either be received from the patient and/or supplied to the patient.

Similar to the embodiment of the patient interface 100 described above, in one embodiment, the nostril interface 214, connecting portion 230, and associated fluid path may be configured to supply a fluid that includes air or oxygen to the patient from a suitable fluid supply, and the nostril interface 216, connecting portion 232 and associated fluid path may be configured to receive a fluid that includes carbon dioxide expired from the patient. In such an embodiment, an internal wall structure, similar to the internal wall structure 138 shown in FIG. 11, may seal the internal conduit 234 communicating with nostril interface 214 from the internal conduit 236 communicating with nostril interface 216. It should also be appreciated that, as described above, any combination of gas delivery and/or gas sampling may be achieved with the patient interface 200.

As shown in FIG. 16, the coupling 218 includes an opening 238 that is configured to allow the internal passageways 215, 217 of the first and second nostril interfaces 214, 216 to communicate with the internal conduits 234, 236 of the coupling 218. In addition, the body portion 212 may include an opening 240 that is configured to allow a portion 242 of the coupling 218 to extend therethrough. The coupling 218 may include a plurality of openings 244 that are configured to allow fluid that is expired by the patient through one or both of the internal passageways 215, 217 of the nostril interfaces 214, 216 to flow from the body portion 212 and directly to atmosphere, rather than through one or both of the connecting portions 230, 232 and into one or both of the associated fluid paths. Such a configuration may allow one or both fluid paths to deliver air or oxygen to the nostril interfaces 214, 216, and also allow carbon dioxide to directly exit the patient interface 200 through the openings 244. It is also contemplated that additional passageways may be provided to the nostril interfaces, similar to the configuration illustrated in FIG. 10, so that the gas to be delivered to the patient and fluid that is expired by the patient may both travel through a single nostril interface.

As shown in FIG. 17, the cover 220 may be formed as a separate piece that may be connected to the nostril interfaces 214, 216 and the body portion 212 either before or after the coupling 218 is connected to the body portion 212. The cover 220 may be formed, e.g., molded, from a soft material having a hardness of less than about 20 durometers Shore 000. In an embodiment, the material may comprise an elastomeric material. In another embodiment, the cover 220 may include a material having a hardness of about 3 to about 5 durometers Shore A, such as silicone rubber. Of course, cover 220 may have a variety of other hardnesses as desired without departing from the spirit or scope of the present invention. In another embodiment, the cover 220 may include a gel material which may be a thermoset or thermoplastic material. It is also contemplated that the cover 220 may be made out of foam or any other comfortable material. Such soft materials may provide comfort to the patient, as the cover is in contact with the patient's skin, both inside the nostril and at an area just above the patient's upper lip.

The cover 220 includes a first generally tubular extension 250 and a second generally tubular extension 252. The first extension 250 has an internal channel 251 that is configured to receive the first nostril interface 214, and the second extension 252 has an internal channel 253 that is configured to receive the second nostril interface 216. The first extension 250 includes an opening 254 at a distal end thereof that is configured to align with the opening 224 of the first nostril interface 214. Likewise, the second extension 252 includes an opening 256 at a distal end thereof that is configured to align with the opening 225 of the second nostril interface 216. This configuration allows the cover 220 to be placed over the body portion 212 and the first and second nostril interfaces 214, 216 and form a frictional fit with the body portion 212, and the first and second nostril interfaces 214, 216.

The first and second extensions 250, 252 are configured to be conformable with the inside surfaces of the patient's nostrils so that when the nostril interfaces 214, 216 and cover 220 are inserted into the patient's nostrils, the cover 220 provides a seal between the nostril interfaces 214, 216 and their respective nostrils, without exerting too much pressure on the patient. The seal may be provided between the cover 220 and an internal surface of the nostril, or an external surface of the nostril located just above the patient's upper lip. The cover 220 includes a portion 260 that is configured extend substantially around one side of the body portion 212 and also configured to engage an area of the patient's skin between the nostril and the upper lip in a similar manner that is illustrated in FIG. 10 and described above with respect to the cover 118 of the patient interface 100. Similar to the previously disclosed embodiments, the present embodiment is configured to direct the fluid flow in a non-longitudinal direction away from the patient's sinuses to enhance comfort. Rather than single openings 224, 225 shown, the openings may extend laterally, from the front, from the back, or at any other location of interfaces 214, 216.

The modularity of the patient interface 200 may provide greater flexibility with respect to the patient. A plurality of body portions 212, couplings 218, and covers 220 may be provided so that particular sizes of each portion may be chosen for the specific patient. Different body portions 212 may include nostril interfaces 214, 216 that have different spacing between them, different lengths, different diameters, different shapes, etc. Similarly, different couplings 218 may have different lengths, and may include or not include the plurality of openings 244, depending on the selected application. In addition, different covers 220 may include extensions 250, 252 that have different spacing between them, different lengths, different diameters, different shapes, different materials, etc. Such a system may provide a more custom and comfortable fit with the patient's particular anatomy. The illustrated embodiment is not intended to be limiting in any way.

Figure 20:
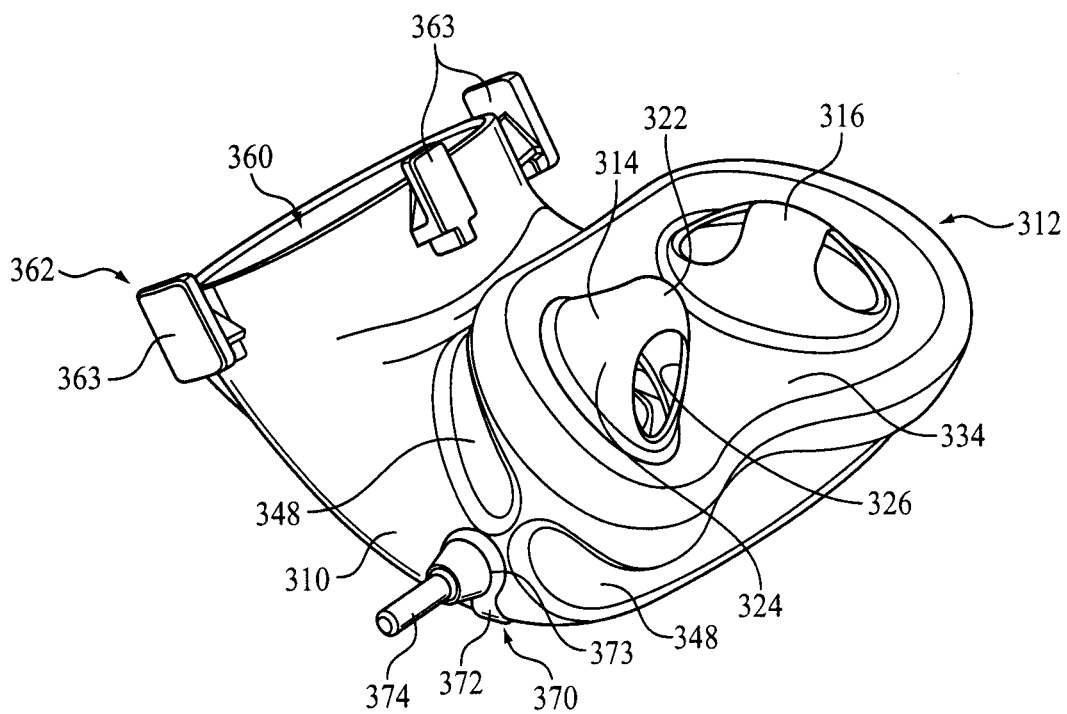
FIG. 20 is a perspective view of a patient interface according to another embodiment of the invention.

FIGS. 20-27 illustrated another embodiment of a patient interface 300 of the present invention. As shown in FIG. 20, the patient interface 300 includes a body portion 310, a seal portion 312 that extends from the body portion 310, a first nostril insertion portion 314 that extends from the seal portion 312, and a second nostril insertion portion 316 that is spaced from the first nostril insertion portion 314 and also extends from the seal portion 312. The body portion 310 defines a fluid passageway 311, or conduit, (see FIG. 21) that is configured to supply fluid to the patient or receive fluid from the patient. Because the first nostril insertion portion 314 and the second nostril insertion portion 316 are of substantially the same design, only the first nostril insertion portion 314 will be discussed further, with the understanding that the second nostril insertion portion 316 may include the same features, unless otherwise indicated herein.

The nostril insertion portion 314 is configured to be inserted into a nostril of a patient. As illustrated, the insertion portion 314 has a distal end 322 and a sidewall 324 that extends from the distal end 322 towards the seal portion 312. In the illustrated embodiment, the sidewall 324 is generally conical in shape, and the distal end 322 is shaped like a rounded tip of a cone. Of course, other shapes of the sidewall are contemplated. For example, the sidewall may be of a tulip shape in which a center portion of the sidewall bulges outwardly, as compared to the tip and base of the sidewall, or the sidewall may be more cylindrical in shape. The illustrated embodiment is not intended to be limiting in any way.

The nostril insertion portion 314 defines a fluid passageway 326, or conduit, that is configured to be in communication with the fluid passageway 311 in the body portion 310 in a similar manner that the passageways 13, 26 illustrated in FIG. 4 are in communication. The fluid passageway 311 in the body portion 310 is configured to be in communication with a fluid path, as discussed in greater detail below, so that the fluid may pass through the passageway 311 and into the passageway 326, or vice-versa. The passageways 311, 326 may be suitably sized so that the gas may be delivered to the patient's nostril at an appropriate pressure for comfortable inhalation, and/or so that carbon dioxide being exhaled by the patient may flow out of the patient interface 300 such that little or no resistance is felt by the patient upon exhalation.

Figure 22:
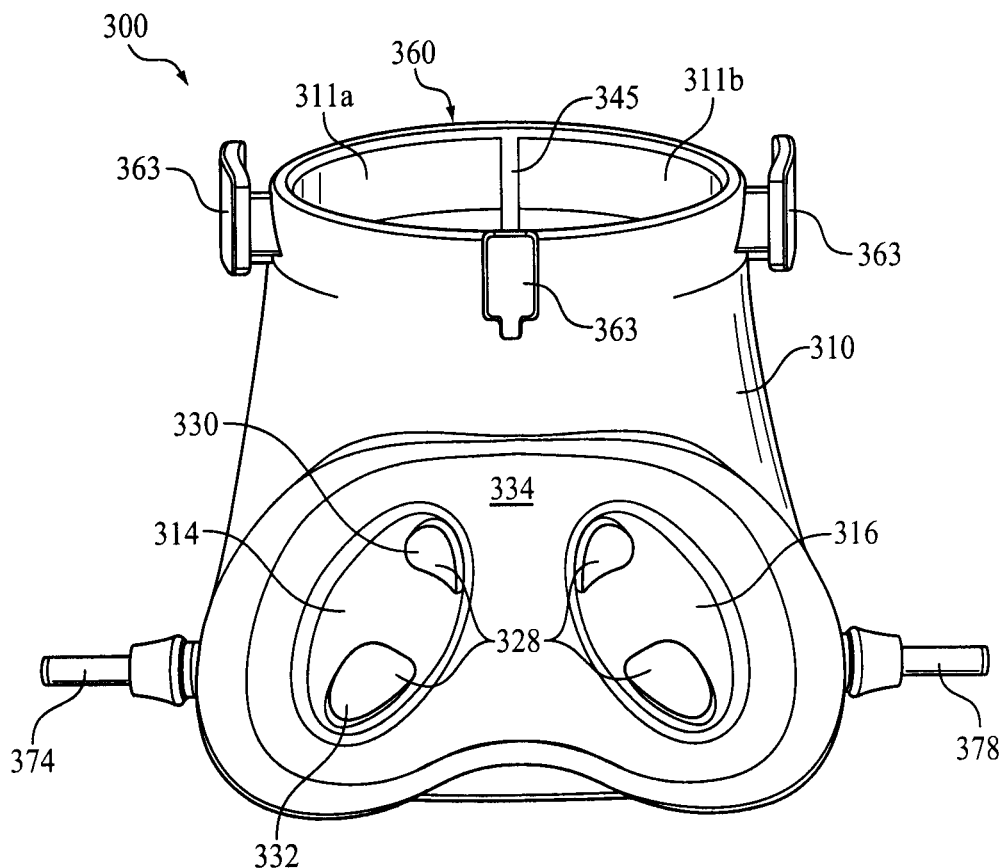
FIG. 22 is a top view of the patient interface of FIG. 20.

As illustrated in FIG. 22, the sidewall 324 of the nostril insertion portion 314 includes at least one laterally directed opening 328 that is configured to communicate fluid between the fluid path and the nostril via the passageways 311, 326. In the illustrated embodiment, the at least one opening 328 is a plurality of openings that include a first opening 330 and a second opening 332 that are located in opposite sides of the insertion portion 314. This configuration allows fluid to be communicated between the fluid path and portions of the nostril that are located on opposite sides, e.g. left and right, of the insertion portion 314. As noted in the previous embodiments, the number, size and location of openings 328 may vary, and are not limited to the configuration illustrated in FIG. 22. Openings 328 may extend from the front, rear, laterally, or any other location in order to enhance comfort and direct the fluid flow in a non-longitudinal direction and away from the patient's sinuses. For example, three openings may be provided in the insertion portion 314 in a similar manner that is illustrated in FIG. 6.

Figure 25:
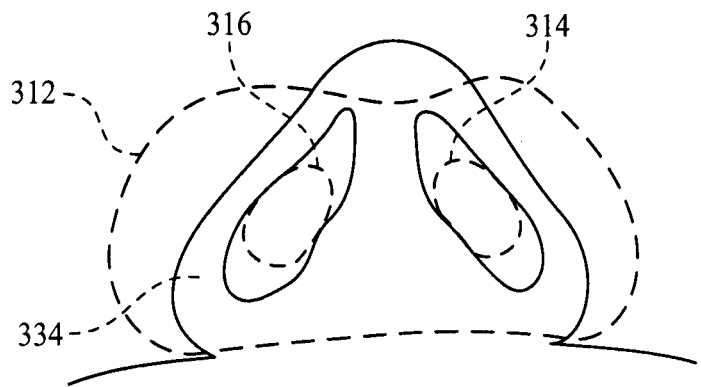
FIG. 25 is a schematic view of the patient interface of FIG. 20 and a patient having a nose of a first shape.
Figure 26:
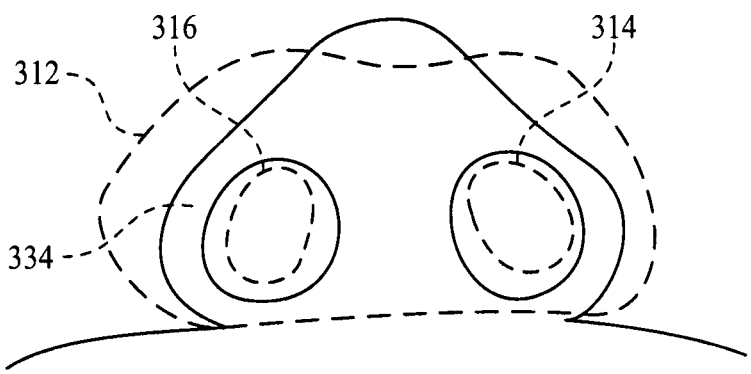
FIG. 26 is a schematic view of the patient interface of FIG. 20 and a patient having a nose of a second shape.
Figure 27:
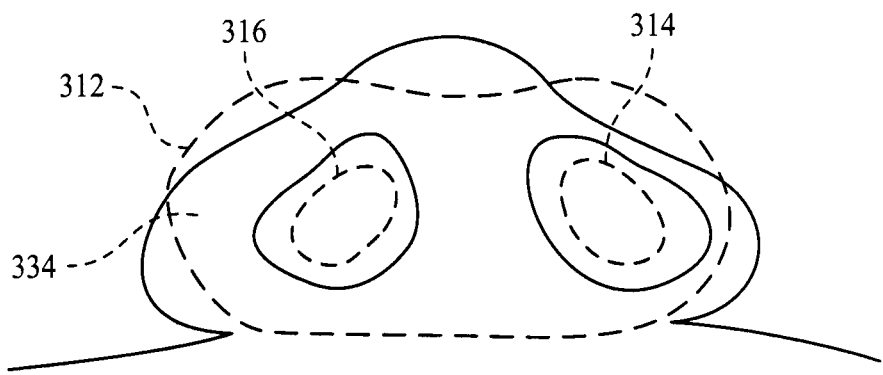
FIG. 27 is a schematic view of the patient interface of FIG. 20 and a patient having a nose of a third shape.

The seal portion 312 is constructed and arranged to provide a seal between the patient interface 300 and the two nostrils of the patient. In the illustrated embodiment, the seal portion 312 includes a continuous, uninterrupted surface 334 that is configured to engage and seal the external lower surfaces of the patient's nostrils. The seal portion 312 may form a base for the insertion portions 314, 316 and may be sized sufficiently large enough to be able to create a seal between the patient interface 300 and a wide variety of shapes of noses. For example, as shown in FIG. 25, the patient may have a nose that is relatively narrow and has relatively narrow nostrils, as compared to the noses illustrated in FIGS. 26 and 27, yet the insertion portions 314, 316 are still able to be inserted into the nostrils and the seal portion 312 is able to create a seal between the seal surface 334 of the patient interface 300 and the nostrils of the patient. Another patient may have nostrils that are relatively rounder, as shown in FIG. 26, than the nostrils of other patients, yet the insertion portions 314, 316 are still able to be inserted into the nostrils and the seal portion 312 is able to create a seal between the seal surface 334 of the patient interface 300 and the nostrils of the patient. By having a continuous, uninterrupted, extended seal surface 334, a single patient interface 300 may be used for multiple nose shapes, because the exterior surface of the nostrils will be able to engage the seal surface 334, regardless of the shape and spacing of the nostrils.

Such a seal should force the fluid that is being supplied through the passageways 311, 326, out of the openings 328, and into the nostrils so that it may be inhaled by the patient, without substantial leaking out of the patient's nostrils and into the surrounding atmosphere. This is because the seal portion 312 should prevent or substantially prevent the fluid from flowing between the patient interface 300 and the nostrils. Similarly, if the patient interface 300 is being used to sample fluid being exhaled by the patient, the fluid should be forced into the openings 328 to escape the nostril, because the seal portion 312 should prevent or substantially prevent the fluid from passing between the nostril and the patient interface 300. Such as arrangement may provide a more efficient design, as less fluid (gas) will be leaked to the surrounding environment.

Figure 21:
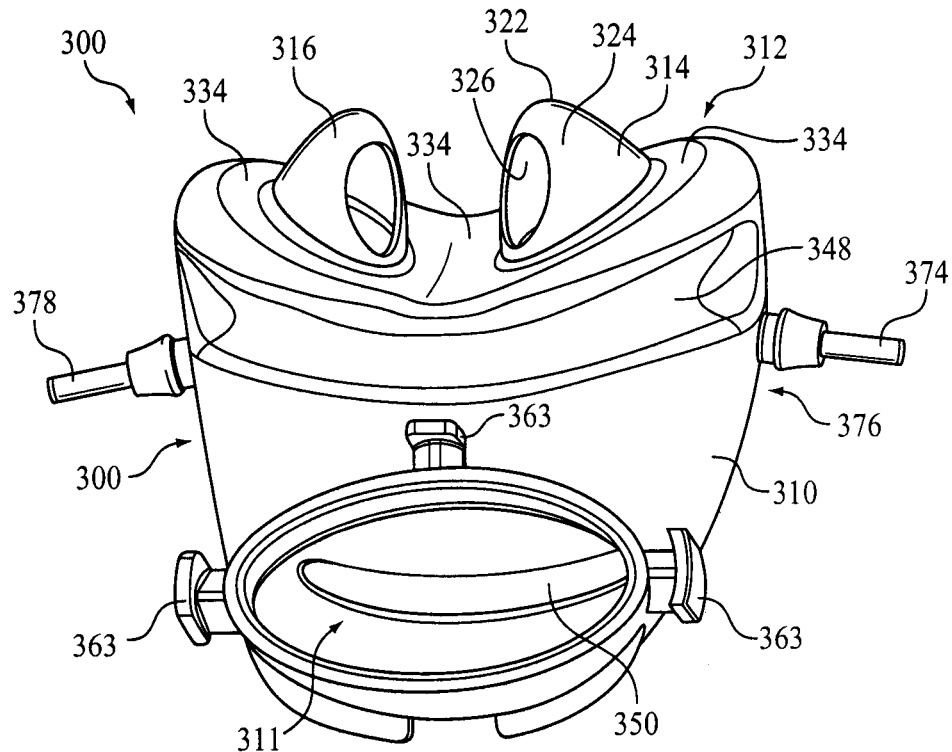
FIG. 21 is another perspective view of the patient interface of FIG. 20.

In an embodiment, illustrated in FIG. 21, the body portion 310 may include a separator 345 that is configured to separate the passageway 311 in the body portion into two passageways 311a, 311b that communicate with the passageway 326 in the first nostril insertion portion 314 and the passageway in the second nostril insertion portion 316, respectively. In this embodiment, the first nostril insertion portion 314 is constructed and arranged to deliver gas from a first fluid path to one nostril of the patient, and the second nostril insertion portion 316 is configured to receive sampled fluid expired from the patient through the other nostril and deliver the expired fluid to a second fluid path. Of course, depending on how the fluid paths are connected to the body portion 310, gas may be delivered to the patient through the second nostril insertion portion 316, and fluid expired from the patient may enter the first nostril insertion portion 314 and be communicated through the body portion 310 to one of the fluid paths.

The body portion 310, the seal portion 312, and the first and second nostril insertion portions 314, 316 may be formed from the same material. Preferably, the body portion 310, the seal portion 312, and the first and second insertion portions 314, 316 are integrally molded from a soft, flexible material, such as an elastomeric material, that provides a comfortable fit with the patient. As shown in greater detail in FIG. 24, the body portion 310 may include at least one flexible section 348 that is constructed and arranged to allow the body portion 310 to be adjusted. Adjustments within the body portion 310 may help to insure that the insertion portions 314, 316 are properly positioned in the patient's nostrils, and the body portion 310 rests comfortably above the patient's upper lip. The flexible section 348 may include a recess or groove 350 that is configured to allow one section of the body portion 310 to pivot relative to another section of the body portion 310. The flexible section 348 may include a malleable material that allows the one section to remain in place relative to the other section once the one section has been pivoted relative to the other section. In another embodiment, the flexible section 348 may be a bellows-type structure, such as those commonly found in plastic drinking straws. The illustrated embodiment is not intended to be limiting in any way. For example, although a plurality of grooves 348 are shown in the Figures, it is contemplated that the grooves 348 may be combined in to a single groove.

Similar to the embodiment illustrated in FIG. 1, the interface 300 also includes a fluid path interface 360 that extends from the body portion 310. The fluid path interface 360 may configured to connect the patient interface 300 to the conduit 66 described above and shown in FIG. 18. In the illustrated embodiment, the fluid path interface 360 includes a locking structure 362 that is configured to lock with the portion 64 of the conduit 66 that defines the fluid path 67. Specifically, the locking structure 362 includes three tabs 363 that are located on one end of the body portion 310, as shown in FIGS. 20 and 21. Each tab 363 is configured to be received by a corresponding sleeve 65 located on the conduit 66. To lock the patient interface 300 to the conduit 66, the tabs 363 are slidingly received by the corresponding sleeves 65. Friction between the tabs 363 and the sleeves 65 holds the tabs 363 within the sleeves 65 until sufficient force is used to pull the tabs 363 out of the sleeves. Of course, other locking arrangements between the patient interface 300 and the conduit 66 may be provided. In addition, other mounting arrangements may be provided. The illustrated embodiments are not intended to be limiting in any way.

Figure 23:
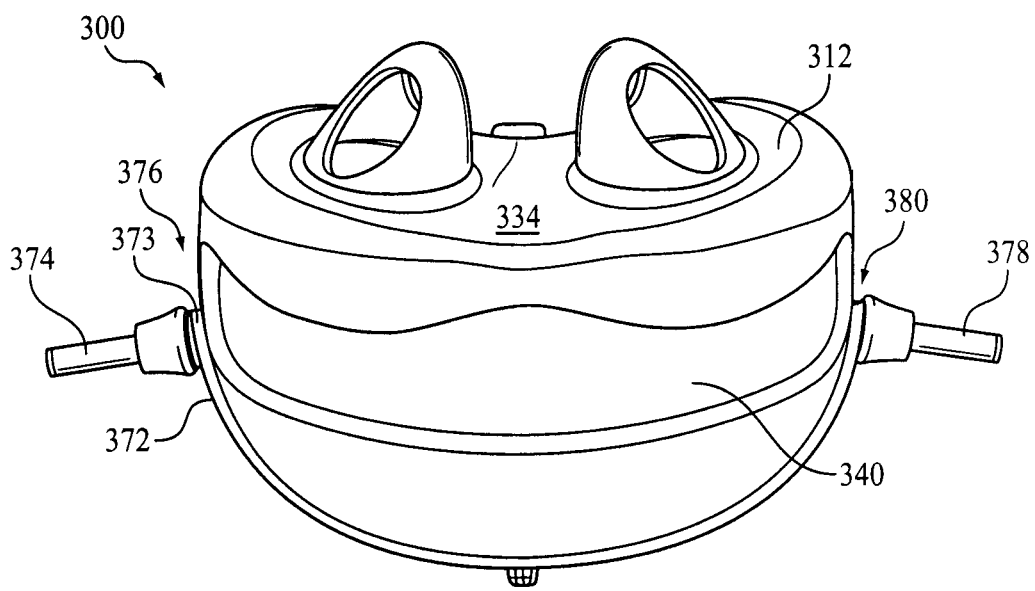
FIG. 23 is a front view of the patient interface of FIG. 20.
Figure 24:
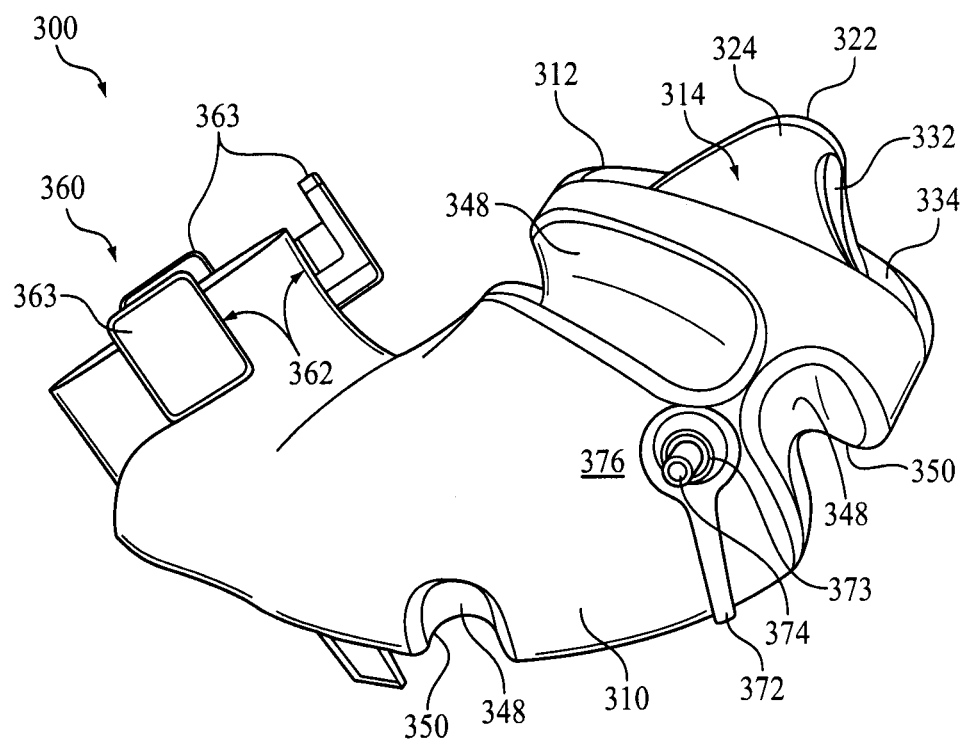
FIG. 24 is a side view of the patient interface of FIG. 20.

In an embodiment, the interface 300 may include an adjustor 370, illustrated in FIGS. 23 and 24, that is configured to adjust the body portion 310 so that an orientation, including position, of the first nostril insertion portion 314 may be adjusted relative to the second nostril insertion portion 316. The adjustor 370 includes a flexible adjustment band 372 that is configured to attach to the body portion 310 on opposite sides thereof, as explained in further detail below. Because the spacing between the nostrils and/or the shape of the nostrils of different patients is different, the orientation of, including the distance between, the nostril insertion portions 314, 316 can be altered based upon the particular patient's nostril spacing.

In the illustrated embodiment, the adjustor 370 also includes a first extension 374 that extends from one side 376 of the body portion 310 and a second extension 378 that extends from an opposite side 380 of the body portion 310. The first extension 374 and the second extension 378 are configured to be connected with the adjustment band 372 so as to hold the adjustment band in tension, which may cause the body portion 310 to flex, thereby adjusting the orientation of one nostril interface relative to the other nostril interface. In the illustrated embodiment, the adjustment band 372 includes a loop 373 at each end thereof that is configured to engage the first and second extensions 374, 378 so that the adjustment band 372 may be held in tension between the extensions 374, 378. If further adjustment is needed, another adjustment band having a different length and/or stretch characteristic may be used instead of or in addition to the adjustment band. For example, if the nostril insertion portions 314, 316 are to be positioned closer together, a shorter adjustment band 372 may be used in comparison with the one illustrated. The adjustment band 372 may be made from any suitable flexible material, including but not limited to an elastomeric material and rubber.

As indicated above, the patient interface 300 illustrated in FIGS. 20-24 may be used as a nasal gas delivery device. In some embodiments, the patient interface may be used as a nasal gas sampling device. Depending on how the fluid paths and internal passageways 311, 326 are configured, the patient interface 300 may be configured to provide gas sampling from one nostril interface and gas delivery to the other nostril interface. It is also contemplated that the nostril interfaces may be configured to provide gas sampling and/or gas delivery to both nostrils with appropriate passageways defined therein, as can be appreciated by those skilled in the art. The above-described and illustrated embodiments are not intended to be limiting in any way.

In use, the patient interfaces described above are particularly well suited for the delivery of gas to a patient. Unlike current patient interfaces that deliver a gas directly up the nasal cavity of the patient, the present invention allows the gas to be directed into a region of the nasal cavity that minimizes the discomfort experienced by the user. For example, the patient interfaces may utilize openings to direct the gas posteriorly and anteriorly within the nasal cavity or utilizes openings to direct the gas laterally. As such, the gas is predominately delivered into the middle and inferior meatus rather than the superior. Of course, the orientation of these openings other than the orientations shown in the figures may be varied without departing from the spirit of the present invention. Each of the interfaces described in the present application are configured to direct the fluid flow towards an appropriate location of the patient's nasal passage and enhance comfort.

In a similar manner, in the embodiment shown in FIGS. 9 and 15, the patient interfaces generally curve inferiorly within the nasal cavity to once again direct the fluid flow towards the middle and inferior meatus and away from the sphenoidal sinuses. Gas delivered into these regions is more efficiently directed into the pharynx and ultimately into the trachea without needlessly being directed upwardly into the frontal and sphenoidal sinuses which would result in needlessly drying out these sinuses and potentially causing discomfort.

One skilled in the art can best appreciate that the features of the various embodiments may be combined with various features from the other embodiments. For instance, the openings of patient interfaces 100, 300 may be incorporated into patient interface 200. Or, the curved configuration of patient interface 200 could be incorporated into patient interfaces 100, and 300. While it has been disclosed in this application that it would be advantageous to direct the delivery of gas towards the middle and inferior meatus, it is also contemplated that it may be advantageous in other applications to direct gas in other directions such as towards the superior meatus, laterally, etc. as dictated by the requirements of a particular application. For example, it may be advantageous to direct the gas towards the superior meatus in order to access the frontal sinus and/or the sphenoidal sinus in the event that the patient interface is being utilized to deliver a gas laden with medication targeted for the frontal and sphenoidal sinuses. The patient interface may be constructed to direct the gas into, or out of a variety of different particular regions of the nasal cavity.

While each of the embodiments are described above in terms of their structural arrangements, it should be appreciated that the present invention also covers the associated methods of using the embodiments described above.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A patient interface comprising:
   a body portion configured to communicate with at least one fluid path;
   at least one at least one nostril interface extending from the body portion, the nostril interface comprising an insertion portion configured to be inserted into a nostril of a patient and to be in communication with the at least one fluid path, the insertion portion comprising at least one opening configured to communicate fluid between the at least one fluid path and the nostril, the at least one opening being directed in a non-axial direction relative to a longitudinal axis of the insertion portion; and
   a seal portion constructed and arranged to provide a seal between the patient interface and the nostril, wherein the insertion portion comprises a distal end and a sidewall extending from the distal end towards the seal portion, wherein the longitudinal axis of the insertion portion extends from the distal end to a plane defined by a top surface of the seal portion, and wherein the at least one opening extends through the sidewall and is directed in a non-axial direction relative to the longitudinal axis of the insertion portion.

2. A patient interface according to claim 1, wherein the seal portion is located between the body portion and the at least one nostril interface.

3. A patient interface according to claim 2, wherein the seal portion is integral with a base of the insertion portion.

4. A patient interface according to claim 3, wherein the seal portion comprises a flange that circumferentially surrounds the base of the insertion portion.

5. A patient interface according to claim 1, wherein the at least one opening comprises two openings disposed on opposite sides of the insertion portion.

6. A patient interface according to claim 1, wherein the at least one fluid path is configured to supply air to the patient.

7. A patient interface according to claim 1, wherein the at least one fluid path is configured to supply oxygen to the patient.

8. A patient interface according to claim 1, wherein the at least one fluid path is configured to receive carbon dioxide from the patient.

9. A patient interface according to claim 1, wherein the body portion and the at least one nostril interface comprise an elastomeric material.

10. A patient interface according to claim 1, wherein the body portion comprises at least one flexible section constructed and arranged to allow the body portion to be adjusted relative to the patient's face.

11. A patient interface according to claim 10, wherein the flexible section comprises a groove.

12. A patient interface according to claim 1, further comprising a fluid path interface extending from the body portion, the fluid path interface being configured to connect the at least one fluid path with the patient interface.

13. A patient interface according to claim 12, wherein the fluid path interface comprises a portion of a locking structure that is configured to lock with another portion of the locking structure disposed on a conduit defining the at least one fluid path.

14. A patient interface according to claim 13, wherein the portion of the locking structure is integral with the fluid path interface.

15. A patient interface according to claim 1, wherein the at least one nostril interface comprises a first nostril interface and a second nostril interface, and further comprising an adjustor for adjusting an orientation of the first nostril interface relative to the second nostril interface.

16. A patient interface according to claim 15, wherein the adjustor comprises a first extension extending from one side of the body portion, a second extension extending from an opposite side of the body portion, and a flexible adjustment band that is constructed and arranged to connect the first extension to the second extension so as to allow adjustment of the first nostril interface relative to the second nostril interface.

17. A patient interface according to claim 16, wherein the adjustment band comprises a first loop at one end thereof configured to be received by the first extension, and a second loop an opposite end thereof configured to be received by the second extension, the adjustment band being constructed and arranged to be in tension when the first loop is connected to the first extension and the second loop is connected to the second extension.

18. A patient interface comprising:
   a body portion configured to communicate with at least one fluid path;
   a seal portion extending from the body portion, the seal portion being constructed and arranged to provide a seal between the patient interface and a first nostril of a patient and to provide a seal between the patient interface and a second nostril of the patient;
   a first nostril insertion portion extending from the seal portion, the first nostril insertion portion comprising at least one laterally directed opening and being constructed and arranged to be inserted into the first nostril of the patient;
   a second nostril insertion portion spaced from the first nostril insertion portion and extending from the seal portion, the second nostril insertion portion comprising at least one laterally directed opening and being constructed and arranged to be inserted into the second nostril of the patient, wherein the seal portion comprises a continuous, uninterrupted surface that is configured to provide the seal between the patient interface and the first and second nostrils of the patient, wherein the first insertion portion and the second insertion portion each comprise a distal end and a sidewall extending from the distal end towards the seal portion, and wherein the at least one laterally directed opening of the first nostril insertion portion extends through the sidewall of the first nostril insertion portion and the at least one laterally directed opening of the second nostril insertion portion extends through the sidewall of the second nostril insertion portion.

19. A patient interface according to claim 18, wherein the at least one opening of the first insertion portion comprises two openings disposed on opposite sides of the first insertion portion, and wherein the at least one opening of the second insertion portion comprises two openings disposed on opposite sides of the second insertion portion.

20. A patient interface according to claim 18, wherein the at least one fluid path is configured to supply air to the patient.

21. A patient interface according to claim 18, wherein the at least one fluid path is configured to supply oxygen to the patient.

22. A patient interface according to claim 18, wherein the at least one fluid path is configured to receive carbon dioxide from the patient.

23. A patient interface according to claim 18, wherein the body portion, the seal portion, and the first and second nostril insertion portions comprise an elastomeric material.

24. A patient interface according to claim 18, wherein the body portion comprises at least one flexible section constructed and arranged to allow the body portion to be adjusted relative to the patient's face.

25. A patient interface according to claim 24, wherein the flexible section comprises a groove.

26. A patient interface according to claim 18, further comprising a fluid path interface extending from the body portion, the fluid path interface being configured to connect the at least one fluid path with the patient interface.

27. A patient interface according to claim 26, wherein the fluid path interface comprises a portion of a locking structure that is configured to lock with another portion of the locking structure disposed on a conduit defining the at least one fluid path.

28. A patient interface according to claim 27, wherein the portion of the locking structure is integral with the fluid path interface.

29. A patient interface according to claim 18, further comprising an adjustor for adjusting an orientation of the first nostril insertion portion relative to the second nostril insertion portion.

30. A patient interface according to claim 29, wherein the adjustor comprises a first extension extending from one side of the body portion, a second extension extending from an opposite side of the body portion, and a flexible adjustment band that is constructed and arranged to connect the first extension to the second extension so as to allow adjustment of the first nostril insertion portion relative to the second nostril insertion portion.

31. A patient interface according to claim 30, wherein the adjustment band comprises a first loop at one end thereof configured to be received by the first extension, and a second loop an opposite end thereof configured to be received by the second extension, the adjustment band being constructed and arranged to be in tension when the first loop is connected to the first extension and the second loop is connected to the second extension.

* * * * *